(12) United States Patent
Dunki-Jacobs et al.

(10) Patent No.: US 9,168,000 B2
(45) Date of Patent: Oct. 27, 2015

(54) MEAL DETECTION DEVICES AND METHODS

(71) Applicant: ETHICON ENDO-SURGERY INC., Cincinnati, OH (US)

(72) Inventors: Adam Dunki-Jacobs, Cincinnati, OH (US); Jason L. Harris, Mason, OH (US); Mathieu Lemay, Bern (CH); Martin Pfleiderer, Auvernier (CH); Martin Proença, Marly (CH); Thierry Utard, Neuchâtel (CH)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 308 days.

(21) Appl. No.: 13/802,089

(22) Filed: Mar. 13, 2013

(65) Prior Publication Data
US 2014/0275748 A1    Sep. 18, 2014

Related U.S. Application Data

(60) Provisional application No. 61/780,013, filed on Mar. 13, 2013.

(51) Int. Cl.
*A61B 5/00* (2006.01)
*A61B 5/053* (2006.01)
(Continued)

(52) U.S. Cl.
CPC ............. *A61B 5/4839* (2013.01); *A61B 5/0537* (2013.01); *A61B 5/4238* (2013.01);
(Continued)

(58) Field of Classification Search
CPC .......... A61B 5/42; A61B 5/01; A61B 5/4866; A61B 5/0488; A61B 5/0024; A61B 5/073; A61B 5/14532
See application file for complete search history.

(56) References Cited

U.S. PATENT DOCUMENTS

| | | |
|---|---|---|
| 4,515,584 A | 5/1985 | Abe et al. |
| 4,823,808 A | 4/1989 | Clegg et al. |

(Continued)

FOREIGN PATENT DOCUMENTS

| | | |
|---|---|---|
| EP | 377695 A1 | 7/1990 |
| WO | 89/011701 A1 | 11/1989 |

(Continued)

OTHER PUBLICATIONS

Habas et al., Metabolic and Cardiovascular Responses to Liquid and Solid Test Meals, British Journal of Nutrition (1998), 79, 241-247.

(Continued)

*Primary Examiner* — Max Hindenburg
(74) *Attorney, Agent, or Firm* — Nutter McClennen & Fish LLP

(57) ABSTRACT

Devices and methods for detecting meal intake are disclosed herein. In some embodiments, one or more sensors can be used to detect or monitor physiological parameters of a user (e.g., heart rate, body movements, temperature, pH, impedance, gastric stretch, sound emissions, and the like). The outputs of the sensors can be received by a computer system configured to analyze the sensor data and make a determination as to whether meal intake has occurred or is presently occurring. The computer system's determination can be used to trigger, modulate, or otherwise control one or more therapeutic devices. Other types of devices can also be controlled using this determination, such as monitoring or logging devices.

18 Claims, 21 Drawing Sheets

(51) Int. Cl.
*A61N 1/36* (2006.01)
*A61F 5/00* (2006.01)
*A61B 7/00* (2006.01)
*A61B 5/01* (2006.01)
*A61B 5/0402* (2006.01)
*A61B 5/0488* (2006.01)
*A61B 5/11* (2006.01)

(52) U.S. Cl.
CPC .......... *A61F5/0013* (2013.01); *A61N 1/36007* (2013.01); *A61B 5/01* (2013.01); *A61B 5/0402* (2013.01); *A61B 5/0488* (2013.01); *A61B 5/04884* (2013.01); *A61B 5/1107* (2013.01); *A61B 5/4836* (2013.01); *A61B 5/4866* (2013.01); *A61B 7/008* (2013.01); *A61B 2505/07* (2013.01); *A61F 2005/002* (2013.01)

(56) References Cited

U.S. PATENT DOCUMENTS

| | | | |
|---|---|---|---|
| 5,188,104 | A | 2/1993 | Wernicke et al. |
| 5,231,988 | A | 8/1993 | Wernicke et al. |
| 5,263,480 | A | 11/1993 | Wernicke et al. |
| 5,398,688 | A | 3/1995 | Laniado |
| 5,540,730 | A | 7/1996 | Terry, Jr. et al. |
| 5,540,734 | A | 7/1996 | Zabara |
| 5,707,400 | A | 1/1998 | Terry, Jr. et al. |
| 6,023,009 | A | 2/2000 | Stegemann et al. |
| 6,572,542 | B1 * | 6/2003 | Houben et al. ................ 600/300 |
| 6,853,862 | B1 | 2/2005 | Marchal et al. |
| 7,191,007 | B2 | 3/2007 | Desai et al. |
| 7,291,721 | B2 | 11/2007 | Giles-Komar et al. |
| 7,330,753 | B2 * | 2/2008 | Policker et al. ............... 600/546 |
| 7,430,450 | B2 | 9/2008 | Imran |
| 7,502,649 | B2 | 3/2009 | Ben-Haim et al. |
| 7,599,743 | B2 | 10/2009 | Hassler, Jr. et al. |
| 7,599,744 | B2 | 10/2009 | Giordano et al. |
| 7,612,182 | B2 | 11/2009 | Giles-Komar et al. |
| 7,664,551 | B2 | 2/2010 | Cigaina |
| 7,914,468 | B2 | 3/2011 | Shalon et al. |
| 8,048,169 | B2 | 11/2011 | Burnett et al. |
| 8,182,442 | B2 | 5/2012 | Grau et al. |
| 8,236,023 | B2 | 8/2012 | Birk et al. |
| 8,239,027 | B2 | 8/2012 | Imran |
| 8,346,399 | B2 | 1/2013 | Blomquist |
| 8,696,616 | B2 * | 4/2014 | Baynham et al. ............... 604/65 |
| 8,934,976 | B2 * | 1/2015 | Wong et al. ..................... 607/41 |
| 2002/0161414 | A1 | 10/2002 | Flesler et al. |
| 2004/0147816 | A1 | 7/2004 | Policker et al. |
| 2005/0038415 | A1 | 2/2005 | Rohr et al. |
| 2005/0065571 | A1 | 3/2005 | Imran |
| 2005/0177067 | A1 | 8/2005 | Tracey et al. |
| 2005/0245986 | A1 | 11/2005 | Starkebaum |
| 2005/0277998 | A1 | 12/2005 | Tracey et al. |
| 2005/0288740 | A1 | 12/2005 | Hassler et al. |
| 2006/0020298 | A1 | 1/2006 | Camilleri et al. |
| 2006/0064037 | A1 | 3/2006 | Shalon et al. |
| 2006/0195146 | A1 | 8/2006 | Tracey et al. |
| 2006/0195153 | A1 | 8/2006 | DiUbaldi et al. |
| 2006/0235448 | A1 | 10/2006 | Roslin et al. |
| 2006/0247719 | A1 | 11/2006 | Maschino et al. |
| 2006/0247721 | A1 | 11/2006 | Maschino et al. |
| 2006/0247722 | A1 | 11/2006 | Maschino et al. |
| 2007/0027483 | A1 | 2/2007 | Maschino et al. |
| 2007/0027484 | A1 | 2/2007 | Guzman et al. |
| 2007/0027492 | A1 | 2/2007 | Maschino et al. |
| 2007/0027498 | A1 | 2/2007 | Maschino et al. |
| 2007/0073361 | A1 | 3/2007 | Goren et al. |
| 2007/0093870 | A1 | 4/2007 | Maschino |
| 2007/0179556 | A1 | 8/2007 | Ben Haim et al. |
| 2007/0185541 | A1 | 8/2007 | DiUbaldi et al. |
| 2007/0203531 | A9 | 8/2007 | Starkebaum |
| 2007/0265598 | A1 | 11/2007 | Karasik |
| 2008/0065168 | A1 | 3/2008 | Bitton et al. |
| 2008/0132962 | A1 | 6/2008 | DiUbaldi et al. |
| 2008/0132968 | A1 | 6/2008 | Starkebaum |
| 2008/0139875 | A1 | 6/2008 | Tracey et al. |
| 2008/0147146 | A1 | 6/2008 | Wahlgren et al. |
| 2009/0062881 | A1 | 3/2009 | Gross et al. |
| 2009/0093858 | A1 | 4/2009 | DiUbaldi |
| 2009/0132018 | A1 | 5/2009 | DiUbaldi et al. |
| 2009/0149918 | A1 | 6/2009 | Krulevitch et al. |
| 2009/0157149 | A1 | 6/2009 | Wahlgren et al. |
| 2009/0192404 | A1 | 7/2009 | Ortiz et al. |
| 2009/0192534 | A1 | 7/2009 | Ortiz et al. |
| 2009/0204132 | A1 | 8/2009 | Ortiz et al. |
| 2009/0240194 | A1 | 9/2009 | Keimel et al. |
| 2009/0264956 | A1 | 10/2009 | Rise et al. |
| 2010/0032443 | A1 | 2/2010 | Mueller et al. |
| 2010/0049274 | A1 | 2/2010 | Cholette |
| 2010/0056948 | A1 | 3/2010 | Hornby et al. |
| 2010/0161001 | A1 | 6/2010 | DiUbaldi et al. |
| 2010/0161005 | A1 | 6/2010 | Wahlgren et al. |
| 2010/0168820 | A1 | 7/2010 | Maniak et al. |
| 2010/0191304 | A1 | 7/2010 | Scott |
| 2010/0211130 | A1 | 8/2010 | Cigaina |
| 2010/0228105 | A1 | 9/2010 | Policker et al. |
| 2010/0234714 | A1 | 9/2010 | Mercier et al. |
| 2010/0239648 | A1 | 9/2010 | Smith et al. |
| 2010/0249677 | A1 | 9/2010 | DiUbaldi et al. |
| 2011/0094773 | A1 | 4/2011 | Bare et al. |
| 2011/0125063 | A1 | 5/2011 | Shalon et al. |
| 2011/0270360 | A1 | 11/2011 | Harris et al. |
| 2012/0089045 | A1 | 4/2012 | Seidl et al. |
| 2012/0172783 | A1 | 7/2012 | Harris et al. |
| 2012/0172792 | A1 | 7/2012 | Baynham et al. |
| 2012/0259427 | A1 | 10/2012 | Graham et al. |
| 2013/0116218 | A1 | 5/2013 | Kaplan et al. |

FOREIGN PATENT DOCUMENTS

| | | |
|---|---|---|
| WO | 02/26101 A2 | 4/2002 |
| WO | 2005/041749 A2 | 5/2005 |
| WO | 2006/034400 A2 | 3/2006 |
| WO | 2006/049725 A2 | 5/2006 |
| WO | 2007/007339 A2 | 1/2007 |
| WO | 2007/092390 A2 | 8/2007 |
| WO | 2008/104982 A2 | 9/2008 |
| WO | 2009/096859 A1 | 8/2009 |
| WO | 2009097542 A2 | 8/2009 |
| WO | 2011/032016 A1 | 3/2011 |
| WO | 2012/091929 A1 | 7/2012 |

OTHER PUBLICATIONS

Abell et al., Electrogastrography. Current assessment and future perspectives. Dig Dis Sci. Aug. 1988;33(8):982-92.

Acharya et al., "Heart rate variability: a review," Med Bio Eng Comput (2006) 44:1031-1051.

Amft et al., Analysis of chewing sounds for dietary monitoring. UbiComp 2005: Proceedings of the 7th International Conference on Ubiquitous Computing. Sep. 2005. Tokyo, Japan. pp. 56-72.

Amft, Automatic dietary monitoring using on-body sensors: Detection fo eating and drinking behaviour in healthy individuals. Dissertation submitted to Chemnitz University of Technology. Germany. 2008. 242 pages.

Amft et al., Methods for detection and classification of normal swallowing from muscle activation and sound. 2006. 10 pages.

Amft et al., On-body sensing solutions for automatic dietary monitoring. Wearable Computing and Healthcare. Persuasive computing 2009. pp. 62-70.

Ahren et al., "Improved meal-related Beta-cell Function and Insulin Sensitivity by the Dipeptidyl Peptidase-IV Inhibitor Vildagliptin in Metformin-treated Patients With Type 2 Diabetes Over 1 Year," Diabetes Care, 2005, 1936-1940.

Barkeling et al., "Vision and Eating Behavior in Obese Subjects," Obesity Research (2003) 11, 130-134.

Brown et al., "Fructose ingestion acutely elevates blood pressure in healthy young humans," Am J Physiol Regal Integr Comp Physiol 924: R730-R737, 2008.

(56) References Cited

OTHER PUBLICATIONS

Buhwald et al., "Baraiatric Surgery: A Systematic Review and Meta-analysis," JAMA, 2004, 1724-1737.

Camilleri et al., "Intra-abdominal vagal blocking (VBLOC therapy): Clinical results with a new implantable medical device," Surgery (2008) vol. 143(6), 723-31.

Codman® 3000 Implantable Constant-Flow Infusion Pump brochure 2003.

Codman® 3000 Implantable Constant-Flow Infusion Pump brochure 2008.

Drucker et al. "The Incretin System: Glucagon-like Peptide-1 Receptor Agonists and Dipeptidyl Peptidase-4 Inhibitors in Type 2 Diabetes," Lancet, 2006, 1696-1705.

Effects of Thickened Feeding on Gastroesophageal Reflux in Infants: A Placebo-Controlled Crossover Study Using Intraluminal Impedance, Pediatrics 111(4), e355-e359 (Apr. 2003).

Friesen et al., "The Effect of a Meal and Water Loading on Heart Rate Variability in Children With Functional Dyspepia," Dig Si Sci 55: 2283-2387 (2010).

Friesen et al., "Autonomic Nervous System Response to a Solid Meal and Water Loading in Healthy Children: Its Relation to Gastric Myoelectrical Activity," Neurogastroenterol Motil. 19(5): 376-382 (2007).

Frokjaer et al. "Gut Sensations in Diabetic Autonomic Neuropathy," Pain, 2007, 320-329.

Gameiro et al. "The Neurotransmitters Glycine and GABA Stimulate Glucagon-like Peptide-1 Release From the GLUTag Cell Line," J Physiol, 2005, 761-772.

Geliebter et al., "Gastric Distension by Balloon and Test-Meal Intake in Obese and Lean Subjects," Am J Clin Nutr, vol. 48, 592-594 (1988).

Gualdi-Russo et al., Influence of various factors on the measurement of multifrequency bioimpedance. HOMO 2002;53 (1):1-16.

Heart rate variability: standards of measurement, physiological interpretation and clinical use. Task Forice of the European Society of Cardiology and the North American Society of Pacing and Electrophysiology. European Heart Journal. 1996;17:354-381.

Hansen et al., "Neural Regulation of Glucagon-like Peptide-1 Secretion in Pigs," Am J Physiol Endocrinol Metab, 2004, E939-947.

Hsiao et al., Accuracy and precision of two in-shoe pressure; measurement systems. Ergonomics. Jun. 20, 2002;45 (8):537-55.;.

International Search Report and Written Opinion for PCT/US2011/065031 dated Feb. 9, 2012.

International Search Report and Written Opinion for PCT/US2011/065034 dated Apr. 12, 2012.

Junker et al., Gesure spotting with body-worn inertial sensors to detect user activites. Nov. 14, 2007. 30 pages.

Kanaley et al., Plasticity of heart rate signalling and complexity with; exercise training in obese individuals with and without type 2 diabetes. Int J; Obes (Lond). Oct. 2009;33(10):1198-206. doi: 10.1038/ijo.2009.145. Epub Aug. 4, 2009.

Iyriboz et al., "Accuracy of pulse oximeters in estimating heart rate at rest and during exercise," Br J Med 1991, 25(3).

Laferrere et al., "Incretin Levels and Effect Are Markedly Enhanced 1 Month After Roux?En?Y Gastric Bypass Surgery in Obese Patients With Type 2 Diabetes," Diabetes Care 30: 1709-1716, 2007.

Lin et al., Postprandial response of gastric slow waves: Correlation of serosal recordings with electrogastrogram. Digestive Diseases and Sciences. Apr. 2000;45(4):645-651.

Lipsitz et al., "Hemodynamic and Autonomic Nervous System Responses to Mixed Meal Ingestion in Healthy Young and Old Subjects and Dysautonomic Patients With Postprandial Hypotension," Circulation, 87: 391-400 (1993).

Lu et al, "Postprandial Changes of Sympathovagal Balance Measured by Heart Rate Variability," Digestive Diseases and Sciences (1999) vol. 44 (4) 857-861.

Lui et al., "Therapeutic Potential of Duodenal Electrical Stimulation for Obesity: Acute Effects on Gastric Emptying and Water Intake," Am J Gastroenterol, 2005, 792-796.

Makeyev, Automatic method of acoustical swallowing detection for monitoring of ingestive behavior. Dissertation. Coulter School of Engineering. Apr. 13, 2010. 126 pages.

Melissas et al., Alterations of Global Gastrointestinal Motility After Sleeve; Gastrectomy: A Prospective Study. Ann Surg. Nov. 15, 2012. Abstract.

Millis et al., Association of body fat percentage and heart rate variability; measures of sympathovagal balance. Life Sci. Jan. 30, 2010;86(5-6):153-7. doi: 10.1016/j.lfs.2009.11.018. Epub Dec. 1, 2009.

Nauck et al., "Release of Glucagon-like Peptide 1 (GLP-1 [7-36 amide]), Gastric Inhibitory Polypeptide (GIP) and Insulin in Response to Oral Glucose After Uppe and Lower Intestinal Restrictions," Zeitschrift fur Gastroenterologie 34: 159-166, 1996.

Nederkoorn et al., "Cephalic phase responses, craving and food intake in normal subjects," Appetite. Aug. 2000; 35 (1):45-55(11).

Nederkoorn et al., "Cue reactivity and regulation of food intake," Eat Behav. 2002 Spring; 3(1):61-72.

Nederkoorn et al., "Exposure to binge food in bulimia nervosa: finger pulse amplitude as a potential measure of urge to eat and predictor of food intake," Appetite. Apr. 2004; 42(2):125-130.

Nolan et al., Sex-based differences in the association between duration of type 2 diabetes and heart rate variability. Diab Vasc Dis Res. Oct. 2009;6(4):276-82.

Niskanen et al., "Software for advanced HRV analysis," Computer Methods and Programs in Biomedicine (2004) 76, 73-81.

Paintal, et al., "A Study of Gastric Stretch Receptors: Their Role in the Peripheral Mechanisms of Satiation of Hunger and Thirst," Journal of Physiology, vol. 126, 255-270 (1954).

Parker et al., Postprandial mesenteric blood flow in humans: relationship to endogenous gastrointestinal hormone secretion and energy content of food. Eur J Gastroenterol Hepatol. May 1995;7(5):435-40. Abstract.

Pumprla et al., "Functional assessment of heart rate variability: physiological basis and practical applications," Intenational Journal of Cardiology 84 (2002) 1-14.

Regional Postprandial Differences in pH Within the Stomach and Gastroesophageal Junction, Digestive Diseases and Sciences, vol. 50, No. 12 (Dec. 2005), pp. 2276-2285.

Reiman et al., "Characterization and Functional Role of Coltage Gated Cation Conductances in the Glucagon-Like Peptide-1 Secreting GLUTag cell line," J Physiol, 2005, 161-175.

Rocca et al, "Role of the Vagus Nerve in Mediating Proximal Nutrient Glucagon-like Peptide-1 Secretion," Endocrinology, 1999, 1687-1694.

Rubino et al., "The Early Effect of the Roux-en-Y Gastric Bypass on Hormones Involved in Body Weight Regulation and Glucose Metabolism," Ann Surg, 2004, 236-242.

Sanmiguel et al., "The TANTALUS TM System for Obesity: Effect on Gastric Emptying of Solids and Ghrelin Plasma Levels," Obesity Surgery vol. 17(11), 1503-09 (2007).

Sazonov et al., Reply to comment on non-invasive monitoring of chewing and swallowing for objective quantification of ingestive behavior. Physiological Measurement. 2009;30:L5-L7.

Sazonov et al., Toward objective monitoring of ingestive behavior in free-living population. Obesity (Silver Spring). Oct. 2009;17(10):1971-5.

Schnabel et al. "Metabolic Effects of the Incretin Exenatide in the Treatment of Type 2 Diabetes," VAS, Health Risk Manag., 2006, 69-77.

Silny et al, "Verification of the intraluminal multiple electrical impedance measurement for the recording of gastrointestinal motility," Nuerogastroenterology & Motility, vol. 5(2): 107-122 (Jun. 1993).

Small et al, "Gut Hormones and the Control of Appetite," Trends Endocrinol Metab, 2004, 259-263.

Spiller et al., "The Ideal Break-inhibition of Jejunal Motility After Ideal Fat Perfusion in Man," Gut, 1984, 365-374.

Task Force of the European Society of Cardiology and the North American Society of Pacing and Electrophysiology, "Heart rate variability," European Heart Journal (1996) 17, 354-381.

(56) References Cited

OTHER PUBLICATIONS

Theodorakis et al., "Human Duodenal Entereoendocrine Cells, Source of Both Incretin Peptides, FLP-1 and CIP," Am J Pysio Endocrinol Metab, 2006, E550-559.
Toft-Nielsen et al., "Determinants of the Impaired Secretion of Glucogon-Like Peptide-a in Type 2 Diabetic Patents," J Clin Endocrinol Metab, 2001, 3717-3723.
Toft-Nielsen et al., "Continuous Subcutaneous Infusion of Glucagon-like Peptide-1 Lowers Plasma Glusoe and Reduces Appetite in Type 2 Diabetic Patents," Diabetes Care, 1999, 1137-1143.
U.S. Appl. No. 12/605,409 filed Oct. 26, 2009.
U.S. Appl. No. 12/980,695 filed Dec. 29, 2010.
U.S. Appl. No. 12/980,710 filed Dec. 29, 2010.
U.S. Appl. No. 12/980,659 filed Dec. 29, 2010.
Vahl et al., "Effects of GLP-1(7-36)NH2, GLP-1(7-37), and GLP-1-(9-36)NH2 on Intravenous Glucose Tolerance and Glucose-induced Insulin Secretion in Healthy Humans," J Clin Endocrinol Metal, 2003 1772-1779.
Vahl et al., "Glucagon-Like Peptide-1 (GLP-1) Receptors Expressed on Nerve Terminals in the Portal Vein Mediate the Effects of Endogenous GLP-1 on Glucose Tolerance in Rats," Endocrinology, 2007, 4965-4973.
Watanabe et al., "Effects of water ingestion on gastric electrical activity and heart rate variability in healthy subjects," J Auton Neuro Syst 58(1 2): 44-50 (1996).
Westerterp-Plentenga et al., Deceleration in cumulative food intake curves, changes in body temperature and diet-induced thermogenesis. Physiol Behav. Dec. 1990;48(6):831-6.
Whitson et al., "Entero?Endocrine Changes After Gastric Bypass in Diabetic and Nondiabetic Patients: A Preliminary Study," J Surg Res 141: 31-39, 2007.
Wu et al., "A Pilot Study to Evaluate the Effect of Splanchic Nerve Stimulation on Body Composition and Food Intake in Rats," Obesity Surgery (2009) vol. 19(11), 1581-85.
Yacin et al., "Pulse rate variability and gastric electric power in fasting and postprandial conditions," 31st Annual International Conference of the IEEE EMBS Minneapolis, MN, Sep. 2-6, 2009.
Yamaguchi et al., Evaluation of gastrointestinal motility by computerized analysis of abdominal auscultation findings. J Gastroenterol Hepatol. Mar. 2006;21(3):510-4.
Yao et al., "Retrograde Gastric Pacing Reduces Food Intake and Delays Gastric Emptying in Humans: A Potential Therapy for Obesity?" Digestive Diseases and Sciences (2005) vol. 50(9), 1569-75.
Yin et al., "Potential of Intestinal Electrical Stimulation for Obesity: A Preliminary Canine Stidy," Obesity, 2007, 1133-1138.
Yin et al., "Inhibitory Effects of Intestinal Electrical Stimulation on Food Intake, Weight Loss, and Gastric Emptying in Rats," Am J Physiol Regul Integr Comp Physiol, 2007, R78-82.
Yin et al., "Inhibitory Effects of Stress on Postprandial Gastric Myoelectrical Activity and Vagal Tone in Healthy Subjects," Neurogastroenterol Motil 16(6): 737-744 (Dec. 2004).
Zhang et al., "Prokineticin 2 is a target Gene of Roneural Basic Helix-loop-helix Factors for Olfactory Bulb Neurogenesis," J Biol Chem, 2007, 6917-6921.
International Search Report and Written Opinion for PCT/US2014/016394 mailed Jul. 18, 2014 (10 pages).

\* cited by examiner

| | |
|---|---|
| 00:00 | CONSENT SUBJECT AND PRESENT PROTOCOL DETAILS |
| 00:05 | COLLECT INFORMATION ABOUT PATIENT (INCLUDING BODY COMP.) |
| 00:10 | CONNECT PATIENT TO DEVICES AND CHECK SIGNALS |
| 00:30 | START RECORDING. WALK ON A TREADMILL |
| 00:45 | FREE ACTIVITY (SITTING AT A DESK) |
| 01:15 | DRINK 1.5 dl OF WATER |
| 01:15 | FREE ACTIVITY (SITTING AT A DESK) |
| 01:45 | DRINK 1.5 dl OF ENERGY DRINK |
| 01:52 | FREE ACTIVITY (SITTING AT A DESK) |
| 02:15 | EAT MEAL (MEASURE BODY COMPOSITION BEFORE AND AFTER) |
| 02:45 | DRINK AT LEAST 1 dl OF HOT BEVERAGE (COFFEE, TEA) |
| 02:52 | FREE ACTIVITY (SITTING AT A DESK) |
| 03:15 | EAT SNACK |
| 03:22 | FREE ACTIVITY (SITTING AT A DESK) |
| 03:45 | DISCONNECT PATIENT FROM DEVICES |
| 03:55 | PERFORM BODY COMPOSITION MEASUREMENTS |
| 04:00 | FINISH |

FIG. 3A

| | |
|---|---|
| 00:00 | CONSENT SUBJECT AND PRESENT PROTOCOL DETAILS |
| 00:05 | COLLECT INFORMATION ABOUT PATIENT (INCLUDING BODY COMP.) |
| 00:10 | CONNECT PATIENT TO DEVICES AND CHECK SIGNALS |
| 00:30 | START RECORDING. WALK ON A TREADMILL |
| 00:45 | FREE ACTIVITY (SITTING AT A DESK) |
| 01:15 | EAT SNACK |
| 01:22 | FREE ACTIVITY (SITTING AT A DESK) |
| 01:45 | DRINK 1.5 dl OF WATER |
| 01:52 | FREE ACTIVITY (SITTING AT A DESK) |
| 02:15 | DRINK 1.5 dl OF ENERGY DRINK |
| 02:22 | FREE ACTIVITY (SITTING AT A DESK) |
| 02:45 | EAT MEAL (MEASURE BODY COMPOSITION BEFORE AND AFTER) |
| 03:15 | DRINK AT LEAST 2 dl OF WATER |
| 03:22 | FREE ACTIVITY (SITTING AT A DESK) |
| 03:45 | DISCONNECT PATIENT FROM DEVICES |
| 03:55 | PERFORM BODY COMPOSITION MEASUREMENTS |
| 04:00 | FINISH |

FIG. 3B $$\text{GLOBAL SENSITIVITY} = \frac{\sum TP}{\sum TP + \sum FN} \qquad \text{GLOBAL SPECIFICITY} = \frac{\sum TN}{\sum TN + \sum FP}$$

| SENSOR | MEAL CATEGORY | GLOBAL SENSITIVITY | GLOBAL SPECIFICITY |
|---|---|---|---|
| EMG | SOLID | 0.97 | 0.98 |
| IMPEDANCE | SOLID | 0.89 | 0.78 |
| ACCELEROMETERS | SOLID + LIQUID | 0.78 | 0.71 |
| MICROPHONE | SOLID + LIQUID | 0.69 | 0.73 |
| TEMPERATURE | DIGESTION | 0.80 | 0.29 |
| HRV | DIGESTION | 0.51 | 0.47 |
| EGG | DIGESTION | 0.56 | 0.47 |

FIG. 12

$$\text{GLOBAL SENSITIVITY} = \frac{\sum TP}{\sum TP + \sum FN} \qquad \text{GLOBAL SPECIFICITY} = \frac{\sum TN}{\sum TN + \sum FP}$$

| SENSORS | MEAL CATEGORY | GLOBAL SENSITIVITY | GLOBAL SPECIFICITY |
|---|---|---|---|
| EMG + ACCEL. | SOLID | 0.96 | 0.98 |
|  | LIQUID | 0.75 | 0.75 |
| IMPED. + ACCEL. | SOLID | 0.88 | 0.77 |
|  | LIQUID | 0.60 | 0.86 |
| EMG + MICRO | SOLID | 0.96 | 0.98 |
|  | LIQUID | 0.53 | 0.79 |
| IMPED. + MICRO | SOLID | 0.88 | 0.78 |
|  | LIQUID | 0.50 | 0.87 |

FIG. 13

MEAL DETECTION DEVICES AND METHODS

CROSS-REFERENCE TO RELATED APPLICATIONS

This application claims priority to U.S. Provisional Application No. 61/780,013 filed on Mar. 13, 2013, which is hereby incorporated by reference herein in its entirety.

FIELD

Devices and methods for detecting meal intake are disclosed herein.

BACKGROUND

A number of therapies exist or are under development which can benefit from detection of meal intake with high sensitivity and/or high specificity. For example, various obesity treatment therapies can be more effective when administered in temporal proximity to or otherwise synchronized with caloric ingestion (e.g., of solid or liquid foods or beverages). Treatment therapies for diabetes and other diseases can also benefit from precise meal detection. Without the ability to accurately detect meal intake, automated therapies are difficult if not impossible to implement.

Individuals or their caregivers can also benefit from an awareness of meal intake timing, patterns, and so forth. It is cumbersome and time consuming, however, to keep track of this information manually.

Accordingly, a need exists for accurate and reliable devices and methods for detecting meal intake.

SUMMARY

Devices and methods for detecting meal intake are disclosed herein. In some embodiments, one or more sensors can be used to detect or monitor physiological parameters of a user (e.g., heart rate, body movements, temperature, pH at one or more points along the gastrointestinal tract, impedance, gastric stretch, sound emissions, and the like). The outputs of the sensors can be received by a computer system configured to analyze the sensor data and make a determination as to whether meal intake has occurred or is presently occurring. The computer system's determination can be used to trigger, modulate, or otherwise control one or more therapeutic devices. Other types of devices can also be controlled using this determination, such as monitoring or logging devices.

In some embodiments, a meal detection system is provided that includes a plurality of sensors, each configured to sense a different physiological parameter of a user, the plurality of sensors being disposed external to the user. The system can also include a processor in communication with the plurality of sensors and configured to analyze outputs of the plurality of sensors to detect meal intake by the user, the processor being further configured to trigger a controlled device to deliver a therapy to the user in response to meal intake detected by the processor. In alternative embodiments, at least one of the sensors can be at least partially disposed within the patient.

The plurality of sensors can be of different types. The processor can be configured, for each of the plurality of sensors, to calculate an index based on the output of the sensor and to determine that meal intake occurred when the index exceeds a threshold value. The processor can be configured to calculate the threshold value by processing a set of training data using an average harmonic mean algorithm, the training data including sensor data for at least one user and ground truth data for the at least one user.

The plurality of sensors can include an electromyograph configured to detect electrical activity of a muscle of the user and the processor can be configured to calculate an electromyograph index based on a number of peaks detected in the electromyograph output. The plurality of sensors can include a microphone configured to detect sounds emitted by the user and the processor can be configured to calculate a microphone index based on frequency matching and temporal matching of the microphone output to a predetermined pattern. The plurality of sensors can include an electrocardiograph configured to detect electrical activity of a heart of the user and the processor can be configured to calculate an electrocardiograph index based on a moving average filtered first derivative of the standard deviation of interbeat intervals in the electrocardiograph output.

The plurality of sensors can include a temperature sensor configured to detect a temperature of the user and the processor can be configured to calculate a temperature sensor index based on a ratio of low frequency components of the first derivative of the temperature sensor output to low frequency components of the standard deviation of the temperature sensor output. The plurality of sensors can include an accelerometer configured to detect motion of the user and the processor can be configured to calculate an accelerometer index based on the total energy of the accelerometer output in a frequency band of interest. The plurality of sensors can include an electrogastrograph configured to detect electrical activity of a digestive system of the user and the processor can be configured to calculate an electrogastrograph index based on the total energy of the electrogastrograph output in a frequency band of interest. The plurality of sensors can include an impedance sensor configured to detect an impedance across a portion of the user and the processor can be configured to calculate an impedance sensor index based on the median energy of the impedance sensor output in a frequency band of interest.

The plurality of sensors can include an electromyograph and an accelerometer, and the processor can be configured to calculate an electromyograph index, an electromyograph threshold value, an accelerometer index, and an accelerometer threshold value. The processor can be configured to determine that solid meal intake occurred when the electromyograph index exceeds the electromyograph threshold value, that liquid meal intake occurred when the electromyograph index does not exceed the electromyograph threshold value and the accelerometer index exceeds the accelerometer threshold value, and that no meal intake occurred when the electromyograph index does not exceed the electromyograph threshold value and the accelerometer index does not exceed the accelerometer threshold value.

The plurality of sensors can include an impedance sensor and an accelerometer, and the processor can be configured to calculate an impedance sensor index, an impedance sensor threshold value, an accelerometer index, and an accelerometer threshold value. The processor can be configured to determine that solid meal intake occurred when the impedance sensor index exceeds the impedance sensor threshold value, that liquid meal intake occurred when the impedance sensor index does not exceed the impedance sensor threshold value and the accelerometer index exceeds the accelerometer threshold value, and that no meal intake occurred when the impedance sensor index does not exceed the impedance sensor threshold value and the accelerometer index does not exceed the accelerometer threshold value.

The plurality of sensors can include an electromyograph and a microphone, and the processor can be configured to calculate an electromyograph index, an electromyograph threshold value, a microphone index, and a microphone threshold value. The processor can be configured to determine that solid meal intake occurred when the electromyograph index exceeds the electromyograph threshold value, that liquid meal intake occurred when the electromyograph index does not exceed the electromyograph threshold value and the microphone index exceeds the microphone threshold value, and that no meal intake occurred when the electromyograph index does not exceed the electromyograph threshold value and the microphone index does not exceed the microphone threshold value.

The plurality of sensors can include an impedance sensor and a microphone, and the processor can be configured to calculate an impedance sensor index, an impedance sensor threshold value, a microphone index, and a microphone threshold value. The processor can be configured to determine that solid meal intake occurred when the impedance sensor index exceeds the impedance sensor threshold value and the microphone index exceeds the microphone threshold value, that liquid meal intake occurred when the impedance sensor index does not exceed the impedance sensor threshold value and the microphone index exceeds the microphone threshold value, and that no meal intake occurred when the impedance sensor index does not exceed the impedance sensor threshold value and the microphone index does not exceed the microphone threshold value.

The system can include a controlled device configured to perform various functions. The controlled device can be configured to at least one of: electrically stimulate tissue of the user, deliver a therapeutic agent to the user, deliver a therapeutic agent configured to provoke a release of one or more hormones from L-cells of the user to trigger ileal brake in the user, deliver insulin to the user, modulate bile acid levels in the user, modulate gastric pH levels in the user, induce an aversive response in the user, stimulate release of GLP-1 in the user, activate brown adipose tissue in the user, adjust a gastric band implanted in the user, control tonal contractions of the user's stomach, adjust a size or volume of a gastric space occupying device implanted in the user, modulate gastric emptying in the user, record a history of the user's meal intake events, and issue an alert to the user or to a caregiver of the user when the user's meal intake exceeds a predetermined threshold or deviates from a predetermined pattern.

In some embodiments, a medical method is provided that includes sensing a plurality of physiological parameters of a user using a plurality of sensors disposed externally to the user and, using a processor in communication with the plurality of sensors, analyzing outputs of the plurality of sensors to detect meal intake by the user. The method can include automatically triggering a controlled device to deliver a therapy to the user in response to meal intake detected by the processor. The delivery of the therapy can be configured to commence with the initiation of the meal, the end of the meal, or at a predetermined time after the start or end of the meal.

The method can include, for each of the plurality of sensors, using the processor to calculate an index based on the output of the sensor and using the processor to determine that meal intake occurred when the index exceeds a threshold value. The method can include using the processor to calculate the threshold value by processing a set of training data using an average harmonic mean algorithm, the training data including sensor data for at least one user and ground truth data for the at least one user.

Said sensing and said analyzing can include at least one of: detecting electrical activity of a muscle of the user using an electromyograph and calculating an electromyograph index based on a number of peaks detected in the electromyograph output, detecting sounds emitted by the user using a microphone and calculating a microphone index based on frequency matching and temporal matching of the microphone output to a predetermined pattern, detecting electrical activity of a heart of the user using an electrocardiograph and calculating an electrocardiograph index based on a moving average filtered first derivative of the standard deviation of interbeat intervals in the electrocardiograph output, detecting a temperature of the user and calculating a temperature sensor index based on a ratio of low frequency components of the first derivative of the temperature sensor output to low frequency components of the standard deviation of the temperature sensor output, detecting motion of the user using an accelerometer and calculating an accelerometer index based on the total energy of the accelerometer output in a frequency band of interest, detecting electrical activity of a digestive system of the user using an electrogastrograph and calculating an electrogastrograph index based on the total energy of the electrogastrograph output in a frequency band of interest, and detecting an impedance across a portion of the user using an impedance sensor and calculating an impedance sensor index based on the median energy of the impedance sensor output in a frequency band of interest.

Triggering the controlled device can include causing the controlled device to at least one of: electrically stimulate tissue of the user, deliver a therapeutic agent to the user, deliver a therapeutic agent configured to provoke a release of one or more hormones from L-cells of the user to trigger ileal brake in the user, deliver insulin to the user, modulate bile acid levels in the user, modulate gastric pH levels in the user, induce an aversive response in the user, stimulate release of GLP-1 in the user, activate brown adipose tissue in the user, adjust a gastric band implanted in the user, control tonal contractions of the user's stomach, adjust a size or volume of a gastric space occupying device implanted in the user, modulate gastric emptying in the user, record a history of the user's meal intake events, and issue an alert to the user or to a caregiver of the user when the user's meal intake exceeds a predetermined threshold or deviates from a predetermined pattern.

Sensing the plurality of physiological parameters can include detecting an impedance across a portion of the user using an impedance sensor having a first current electrode, a second current electrode, a first voltage electrode, and a second voltage electrode. The method can include positioning the first current electrode on the user's left trapezius muscle, positioning the second current electrode on the user's right trapezius muscle, positioning the first voltage electrode on the user's chest below the user's left clavicle and about half way between the user's neck and the user's left shoulder, and positioning the second voltage electrode on the user's chest below the user's right clavicle and about half way between the user's neck and the user's right shoulder. Alternatively, or in addition, the method can include positioning the first current electrode on the user's chest below the user's left clavicle and about half way between the user's neck and the user's left shoulder, positioning the second current electrode on the user's chest below the user's right clavicle and about half way between the user's neck and the user's right shoulder, positioning the first voltage electrode beneath the first current electrode and inward towards the user's sternum, and positioning the second voltage electrode beneath second current electrode and inward towards the user's sternum.

The present invention further provides devices and methods as claimed.

BRIEF DESCRIPTION OF THE DRAWINGS

The invention will be more fully understood from the following detailed description taken in conjunction with the accompanying drawings, in which:

FIG. 3A is an exemplary protocol for use in obtaining training data for calibrating the meal detection system of FIG. 1;

FIG. 3B is another exemplary protocol for use in obtaining training data for calibrating the meal detection system of FIG. 1;

FIG. 12 is a table of sensitivity and specificity for various sensors and meal categories;

FIG. 13 is a table of sensitivity and specificity for various sensor combinations and meal categories;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Introduction

Devices and methods for detecting meal intake are disclosed herein. In some embodiments, one or more sensors can be used to detect or monitor physiological parameters of a user (e.g., heart rate, body movements, temperature, pH at one or more points along the gastrointestinal tract, impedance, gastric stretch, sound emissions, and the like). The outputs of the sensors can be received by a computer system configured to analyze the sensor data and make a determination as to whether meal intake has occurred or is presently occurring. The computer system's determination can be used to trigger, modulate, or otherwise control one or more therapeutic devices. Other types of devices can also be controlled using this determination, such as monitoring or logging devices.

Such devices and methods can be used to trigger automated or manual therapies for treating a user. In some embodiments, therapy can be administered to the user for a limited period of time such that the user stops receiving the therapy prior to a second onset of meal intake, e.g., the user beginning a second eating session, which can trigger a second delivery of the therapy to the user for a limited period of time. In other words, the user can intermittently receive therapy throughout a period of hours, days, weeks, months, etc., with each delivery of the therapy coinciding with meal intake. By providing therapy in conjunction with eating and/or drinking, the therapy can be most effective in treating a user condition and/or encouraging weight loss. Accurate meal detection provided by such devices and methods can be an important baseline prerequisite for automated or semi-automated therapies, including obesity and insulin treatment therapies, as well as others. Therapies for metabolic disorders can also be more effective if coordinated with meal intake.

References herein to "meal ingestion" or "meal intake" can include ingestion of solid foods, liquid foods, beverages, snacks, and so forth, whether caloric or otherwise.

System Generally

Figure 1:
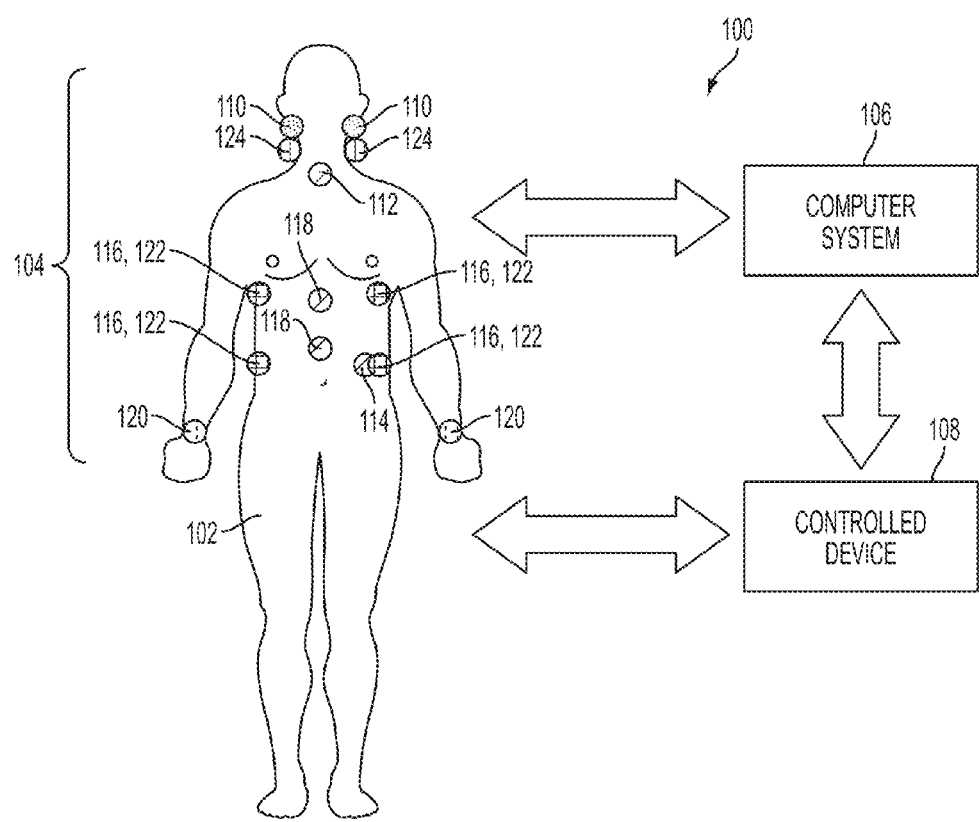
FIG. 1 is a schematic diagram of a controlled device and a meal detection system having a plurality of sensors coupled to a user.

FIG. 1 illustrates an exemplary embodiment of a meal detection system 100 for detecting meal intake by a user 102. The system 100 generally includes one or more sensors 104 configured to sense physiological parameters of the user 102 and a computer system 106 configured to process and interpret the outputs of the one or more sensors to make a determination as to whether meal intake has occurred or is presently occurring. Each sensor 104 can monitor different physiological parameters of the user. A controlled device 108 can be coupled to the meal detection system 100 such that the meal detection system is configured to trigger, modulate, or otherwise control the controlled device 108 based on determinations made by the computer system 106.

The sensors 104, the computer system 106, and the controlled device 108 can all be implanted within the user 102, can all be positioned external to the user, or some can be implanted while others are positioned externally. For example, some components can be positioned subcutaneously while others are positioned transcutaneously. Components of the system which are implanted can be powered using an implanted power source or can be powered remotely, for example as disclosed in U.S. Pat. No. 7,599,743 filed Jun. 24, 2004 entitled "Low Frequency Transcutaneous Energy Transfer To Implanted Medical Device." The computer system 106 can be configured for implantation in the user, for example by including a hermetically-sealed biocompatible coating. The computer system 106 can also be configured to be worn or carried by the user, for example by integrating the computer system 106 with an article of clothing or other accessory. The computer system 106 can be, or can be included in, a portable computer, a desktop computer, a hand-held electronic device such as a mobile phone, etc., as will be appreciated by a person skilled in the art. It will be appreciated that any combination of the sensors 104, the computer system 106, and the controlled device 108 can be integrated into a single physical device, housing, package, or system.

The computer system 106 can be directly coupled to the sensors 106 and the controlled device 108, e.g., using electrically-conducive wires or leads, or can be wirelessly coupled thereto using various protocols known in the art. Sensor data can be transmitted to the computer system 106 in real time. The computer system 106 can also be configured to send instructions to the sensors 104, for example to reset or calibrate the sensors, or to instruct the sensors to take a measurement.

Computer System

Figure 2:
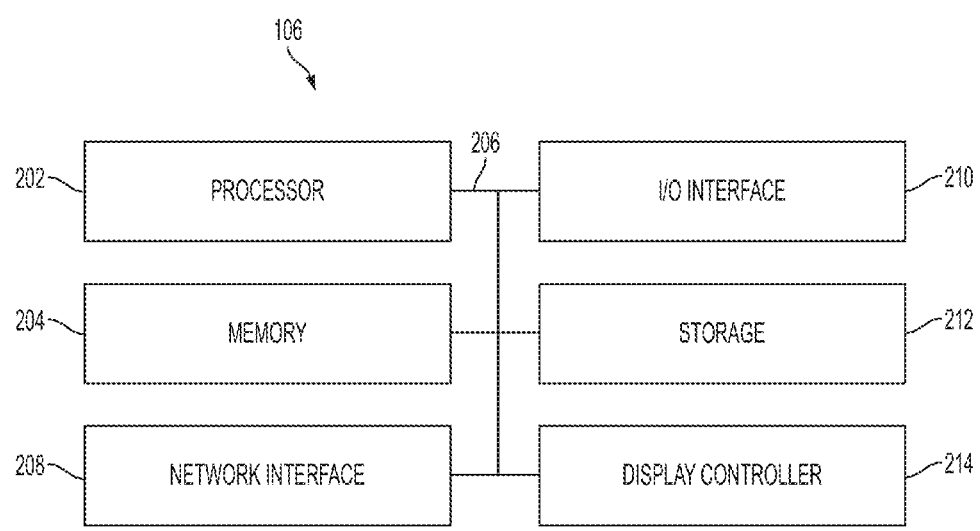
FIG. 2 is a schematic diagram of a computer system of the meal detection system of FIG. 1.

FIG. 2 illustrates an exemplary architecture of the computer system 106. Although an exemplary computer system 106 is depicted and described herein, it will be appreciated that this is for sake of generality and convenience. In other embodiments, the computer system may differ in architecture and operation from that shown and described here. For example, a system on chip (SOC) architecture can be used to decrease the size of the computer system and increase its portability and/or implantability.

The illustrated computer system 106 includes a processor 202 which controls the operation of the computer system 106, for example by executing an operating system (OS), device drivers, application programs, and so forth. The processor 202 can include any type of microprocessor or central processing unit (CPU), including programmable general-purpose or special-purpose microprocessors and/or any of a variety of proprietary or commercially-available single or multi-processor systems. The computer system 106 also includes a memory 204, which provides temporary or permanent storage for code to be executed by the processor 202 (e.g., programs being configured to cause the computer system 106 to perform one or more steps) or for data that is processed by the processor 202. The memory 204 can include read-only memory (ROM), flash memory, one or more varieties of random access memory (RAM), and/or a combination of memory technologies. The various elements of the computer system 106 are coupled to a bus system 206. The illustrated bus system 206 is an abstraction that represents any one or more separate physical busses, communication lines/interfaces, and/or multi-drop or point-to-point connections, connected by appropriate bridges, adapters, and/or controllers.

The computer system 106 also includes a network interface 208, an input/output (I/O) interface 210, a storage device 212, and a display controller 214. The network interface 208 enables the computer system 106 to communicate with remote devices (e.g., other computer systems) over a network. The I/O interface 210 facilitates communication between one or more input devices (e.g., the sensors 104), one or more output devices, and the various other components of the computer system 106. The storage device 212 can include any conventional medium for storing data and programs in a non-volatile and/or non-transient manner. The storage device 212 can thus hold data and/or instructions in a persistent state (i.e., the value is retained despite interruption of power to the computer system 106). The storage device 212 can include one or more hard disk drives, flash drives, USB drives, optical drives, various media disks or cards, and/or any combination thereof and can be directly connected to the other components of the computer system 106 or remotely connected thereto, such as over a network. The display controller 214 includes a video processor and a video memory, and generates images to be displayed on one or more displays in accordance with instructions received from the processor 202.

The various functions performed by the meal detection system 100 can be logically described as being performed by one or more modules. It will be appreciated that such modules can be implemented in hardware, software, or a combination thereof. It will further be appreciated that, when implemented in software, modules can be part of a single program or one or more separate programs, and can be implemented in a variety of contexts (e.g., as part of an operating system, a device driver, a standalone application, and/or combinations thereof). In addition, software embodying one or more modules can be stored as an executable program on one or more non-transitory computer-readable storage mediums. Functions disclosed herein as being performed by a particular module can also be performed by any other module or combination of modules, and the meal detection system 100 can include fewer or more modules than what is shown and described herein.

It will be appreciated that sensor data can be communicated to the computer system 106 instantaneously or near-instantaneously. The computer system 106 can thus analyze relatively recent data and relatively quickly begin analysis thereof, as will be appreciated by a person skilled in the art. In this way, the computer system 106 can make a relatively quick determination as to whether the user has begun ingesting a meal. This in turn can be used to trigger the controlled device 108 in a relatively quick manner. In other words, if the computer system 106 determines from the gathered data that the user started ingesting a meal, delivery of a therapy to the user can be automatically initiated relatively soon after the onset of meal intake.

The computer system 106 can perform various signal processing functions with respect to the sensor data to make the data more suitable for meal intake determinations or for calculating a measurement index for assessing whether meal intake has likely occurred, e.g., as detailed below with respect to each sensor type. The computer system 106 can include a meal intake determination module configured to make a determination as to whether meal intake has occurred or is presently occurring. The meal intake determination module can also be configured to determine or estimate the size of the meal, for example based on the signal count or pattern of one or more sensor outputs, e.g., an electromyograph, an impedance sensor, and/or an accelerometer. Any of a variety of algorithms can be used to make the meal intake determination based on sensor data received by the computer system 106.

In some embodiments, the determination algorithm can include comparing an index value calculated for a particular sensor over a particular window of time to a predetermined threshold value. Index values for a plurality of sensors can also be considered together in making the meal intake determination. Further details on determination algorithms are provided below.

Sensors

Generally, the sensors 104 can be configured to gather data from the user 102 regarding one or more physiological parameters of the user, and each sensor typically gathers data for a different physiological parameter. The sensors 102 can be in communication with the computer system 106 such that the sensors communicate sensed data to the computer system 106 for processing. A number of exemplary sensors are described below.

An externally-located sensor can allow for meal detection and therapy triggering without requiring surgery to implant the sensor, thereby reducing, if not eliminating, adverse side effects and potential complications from surgery. If a controlled device configured to be triggered based on data gathered by an externally-located sensor is also transcutaneously positioned, e.g., in the form of a transdermal patch configured to electrically stimulate the user, then the user can be effectively treated without requiring any surgery, thereby eliminating adverse side effects and potential complications from surgery. However, it will be appreciated that the sensors 104 can also be implanted in the user as part of a surgical procedure (e.g., a surgical procedure to treat severe obesity).

A plurality of sensors can be used simultaneously to inform the meal intake determination, providing redundancy in case of sensor and/or communication failure, and increasing accuracy in determining that meal intake has occurred or is occurring. For example, sensor combinations can be used in which one sensor is very effective at detecting one type of activity (e.g., eating solid food) and another sensor is very effective at detecting a different type of activity (e.g., drinking or exercise) such that the combination of sensors provides a synergistic improvement in meal detection accuracy.

In some embodiments, a measurement index can be calculated for each sensor or for each sensor type and can be compared to a threshold value to inform a meal intake determination. While a number of exemplary index types and threshold values are disclosed below, it will be appreciated that other index types or threshold values can be used depending on the particular application and its sensitivity and specificity requirements and other factors.

Threshold values can be determined empirically by monitoring one or more subjects as they perform various activity protocols. Exemplary protocols are illustrated in FIGS. 3A and 3B. Sensor data can be captured during the protocols along with an individual ground truth for each subject (e.g., a log of when the subject is actually chewing, swallowing, or digesting). This training data can be divided into a plurality of time segments (e.g., segments of 5 minutes each). The number of true positives (TP), true negatives (TN), false positives (FP), and false negatives (FN) can be calculated, along with the equivalent sensitivity (TP/(TP+FN)) and specificity (TN/(TN+FP)). A sensitivity value SE(n, T) and specificity value SP(n, T) can be determined for each possible threshold value T and for each subject n in the training set. An average harmonic mean of the sensitivity and specificity can be calculated to determine an ideal threshold value for the sensor that optimizes specificity and sensitivity. Average harmonic mean of sensitivity SE(n, T) and specificity SP(n, T) can be calculated according to:

$$H(T) = \frac{1}{N}\sum_{n=1}^{N} \frac{2 \cdot SE(n, T) \cdot SP(n, T)}{SE(n, T) + SP(n, T)},$$

where n represents the subject index, T is the determination threshold value, and N is the number of subjects in the training set. The maximum value of T in the function H(t) can be used as the determination threshold for the sensor. Threshold values for each sensor type can be determined empirically and stored in the memory 204 of the computer system 106 during manufacturing for subsequent use with all users of the system 100.

Alternatively, or in addition, user-specific thresholds can be used. For example, a training set can consist solely of the individual end-user of the meal detection system 100. The meal detection system 100 can thus be operable in a training mode in which sensor data is recorded and the user provides ground truth information to the computer system 106 (e.g., by manually signaling to the meal detection system 100 when meal intake is occurring, and optionally the type and volume of the meal intake). This information can be used by the computer system 106 as described above to define thresholds for each sensor that are tailored to the individual user. Later, when the meal detection system 100 is no longer operating in the training mode, these thresholds can be used to automatically detect meal intake without requiring additional user input. Reference is made herein to various sensor outputs or indexes "exceeding" a threshold. It will be appreciated that "exceeding" a threshold can, in some instances, be understood to mean crossing a threshold. In other words, a value that is numerically less than a threshold value can be considered to "exceed" the threshold when the threshold is defined such that values which are numerically less than the threshold are considered a trigger. For example, if a threshold is defined as "trigger when less than 7," then a value of 3 can be said to "exceed" the threshold.

Electromyographs (EMG)

The one or more sensors 104 can include an electromyograph ("EMG") configured to sense or detect electrical potential of one or more of the user's muscles. The electromyograph can generate an output signal that represents the muscle's electrical potential as a function of time. The electromyograph can include surface leads or electrodes configured for attachment to the user's skin and/or intramuscular leads or electrodes configured to be placed within the observed muscles, e.g., in the form of needles or wires. In some embodiments, the electromyograph can have a sampling rate of about 312.5 Hz. Exemplary electromyographs include the Biopac MP150 Data Acquisition System and the Biopac 100C Biopotential Amplifier available from Biopac Systems, Inc.

The electromyograph electrodes can be coupled to, or configured to measure, various muscles or muscle groups of the user. For example, as shown in FIG. 1, the electromyograph electrodes 110 can be coupled to the user's jaw muscles (e.g., the masseter, the temporalis, the sphenomandibularis, the medial pterygoid, the lateral pterygoid, the hyoid, and/or the sternohyomastoid). Alternatively, or in addition, the electromyograph electrodes can be coupled to other muscles, such as the user's neck muscles or abdominal muscles. Each time the monitored muscles are fired (e.g., the jaw muscles when chewing food), a peak can be generated in the electromyograph output. Information representing the number of peaks that occur in a certain period of time or the amplitude/intensity of the peaks can be used for meal detection purposes.

Figure 4A:
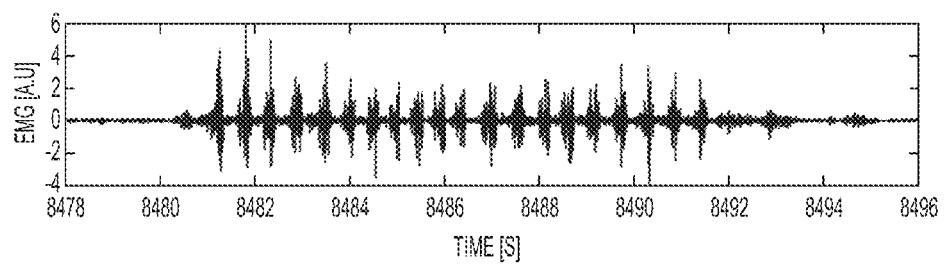
FIGS. 4A-4G illustrate an exemplary method of calculating an index for an electromyograph.

The electromyograph output can be received by the computer system 106 and can be conditioned and otherwise processed to detect meal intake by the user. FIG. 4A illustrates an exemplary raw output signal generated by the electromyograph and communicated to the computer system 106. The computer system 106 can analyze the sensor output in segments that correspond to discrete windows of time. For example, the computer system 106 can record the sensor output for a predetermined time period (e.g., 10 seconds, 30 seconds, 1 minute, 5 minutes, 10 minutes, etc.) and, at the conclusion of the predetermined time period or thereafter, analyze the sensor output corresponding to that time period.

Figure 4B:
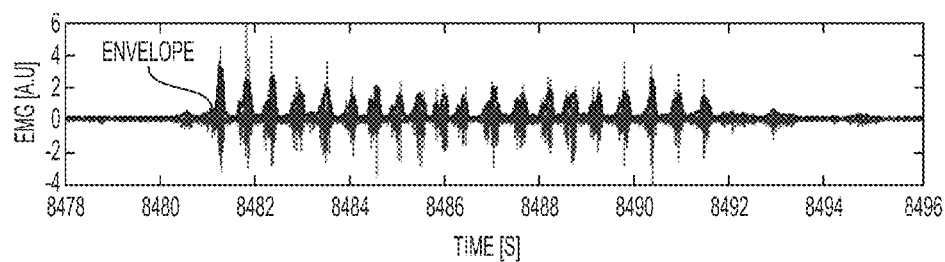
Figure 4C:
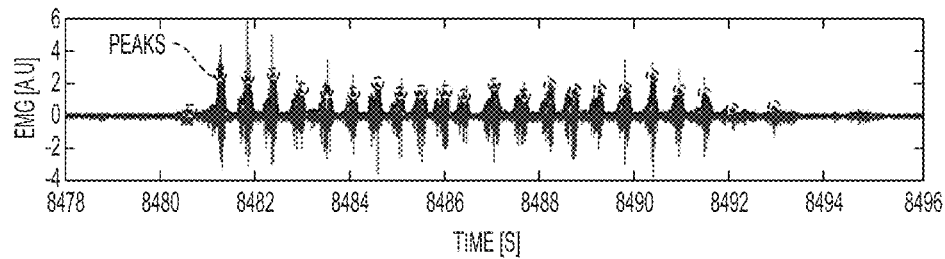
Figure 4D:
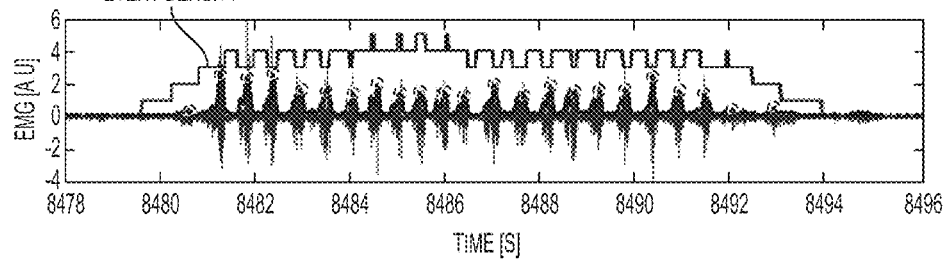

The computer system 106 can perform envelope extraction to produce an estimated superior envelope of the raw electromyograph signal for the time period under consideration, as shown in FIG. 4B. The computer system 106 can then perform peak detection (FIG. 4C) and event density (FIG.

Figure 4E:
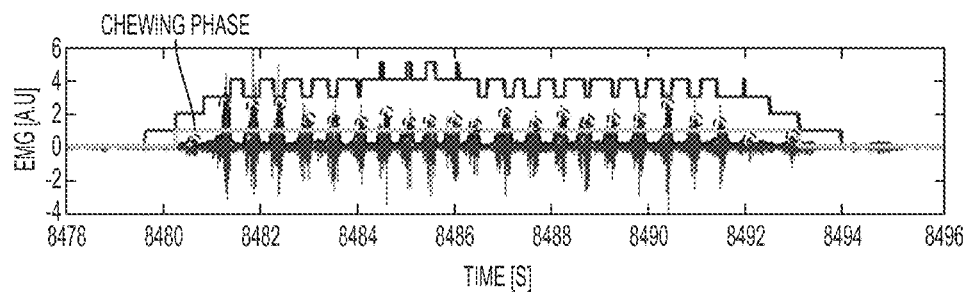
Figure 4F:
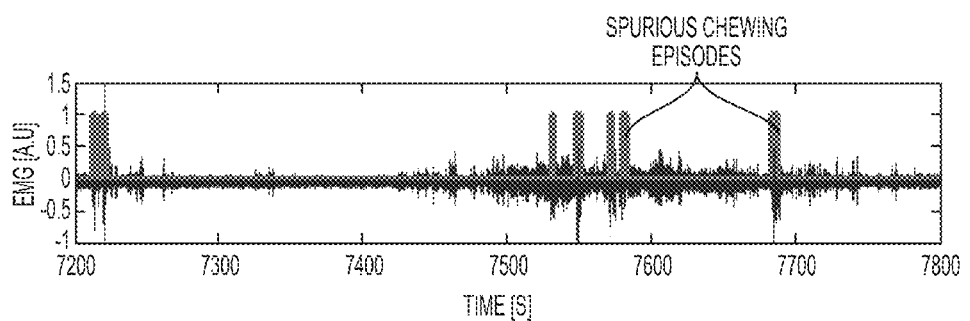

4D) processing. As shown in FIG. 4E, the computer system 106 can extract a chewing phase from the processed data. Chewing episodes associated with meal intake are typically characterized by multiple, rhythmic chewing events. Accordingly, spurious chewing episodes, shown in FIG. 4F, can be excluded from the data using an index that is the ratio of the number of detected peaks to the variance of the inter-peak intervals.

Figure 4G:
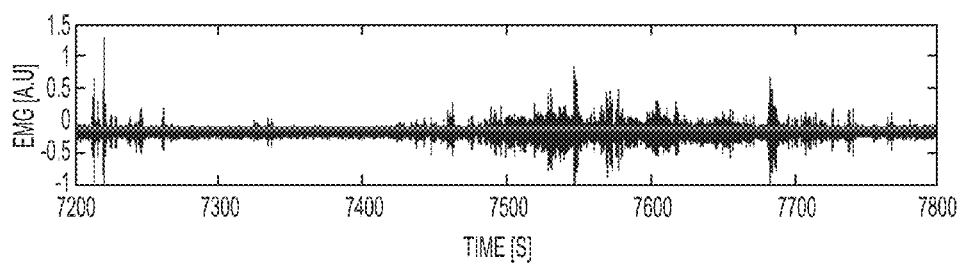

Time periods in which the electromyograph output produces an index value below the threshold amount can be excluded as not involving meal intake. Thus, as shown in FIG. 4G, the spurious chewing events of FIG. 4F can be ignored. Time periods in which the electromyograph output produces an index values greater than or equal to the threshold can be interpreted as meal intake by the user or, as discussed below, can be used in conjunction with other data to make such an interpretation. In some embodiments, the threshold index value can be about 43. Accordingly, peak-detection based processing can be used to detect chewing events from the electromyograph output.

Microphones

The one or more sensors can include a microphone configured to sense or detect sounds generated or emitted by the user. A variety of microphone types can be used, including condenser microphones, dynamic microphones, ribbon microphones, carbon microphones, piezoelectric microphones, fiber optic microphones, laser microphones, liquid microphones, and MEMS microphones. The microphone can include an acoustic-to-electric transducer that converts sounds generated by the user into an electrical output signal.

The microphone transducer can be configured for attachment to the user's skin or clothing, or can be implanted in the user. In some embodiments, the microphone can have a sampling rate of about 44,100 Hz. Exemplary microphones include the NT3 Throat Microphone System available from IASUS Concepts Ltd.

The microphone can coupled to, aimed at, or disposed in proximity to various portions of the user. For example, as shown in FIG. 1, a first microphone 112 can be coupled to the user's throat and a second microphone 114 can be coupled to the user's abdomen in the vicinity of the user's stomach. The first microphone can detect sounds emitted by the user's throat when the user is swallowing. The second microphone can detect sounds emitted by the user's gastrointestinal system as food or beverages are digested. When such sounds are detected, a signature pattern can be generated in the microphone output. Information representing the number of patterns that occur in a certain period of time or the amplitude/intensity of the patterns can be used for meal detection.

The microphone output can be received by the computer system 106 and can be conditioned and otherwise processed to detect meal intake by the user. The computer system 106 can analyze the microphone output in segments that correspond to discrete windows of time. For example, the computer system 106 can record the microphone output for a predetermined time period (e.g., 10 seconds, 30 seconds, 1 minute, 5 minutes, 10 minutes, etc.) and, at the conclusion of the predetermined time period or thereafter, analyze the microphone output corresponding to that time period.

Figure 5A:
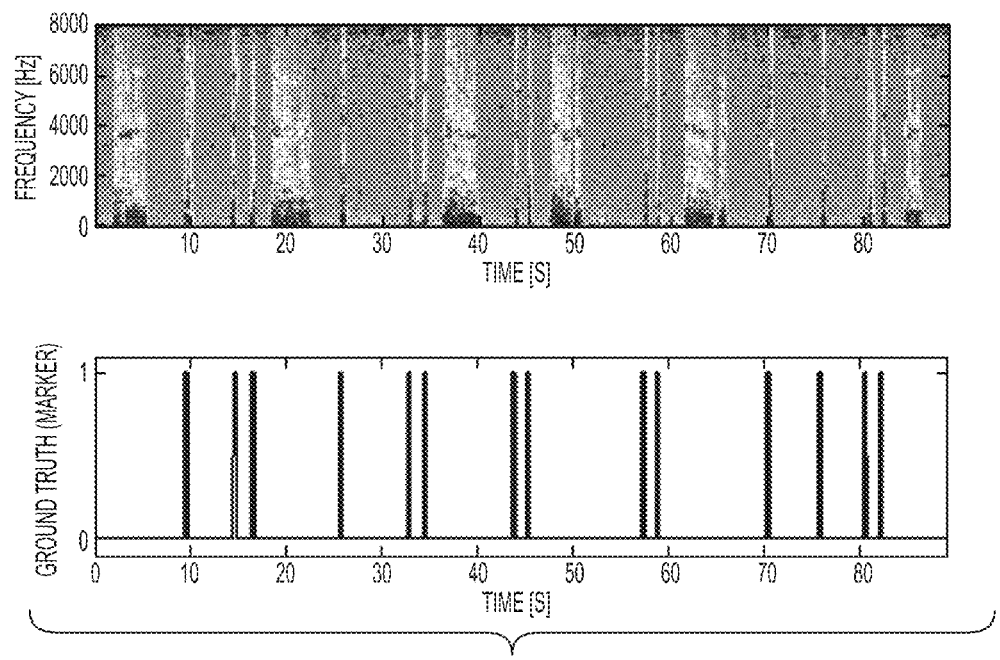
FIGS. 5A-5D illustrate an exemplary method of calculating an index for a microphone.

FIG. 5A is time-frequency spectrogram that exemplifies the output of a throat microphone during a period that includes plural swallowing events, shown with a corresponding ground truth plot. As shown, a discernable pattern coincides with each swallowing event. In the illustrated embodiment, the pattern is characterized by short duration episodes of a large frequency band. The computer system 106 can perform various signal processing routines to condition the raw microphone output. For example, notch filters can be used to eliminate noise in a particular frequency band and its harmonics. A non-linear spatial filter can be used to make the frequency pattern more pronounced. A spectrogram applied to the filtered output can be normalized to diminish the effect of residual noise, for example by normalizing the power over the entire spectrogram.

Figure 5B:
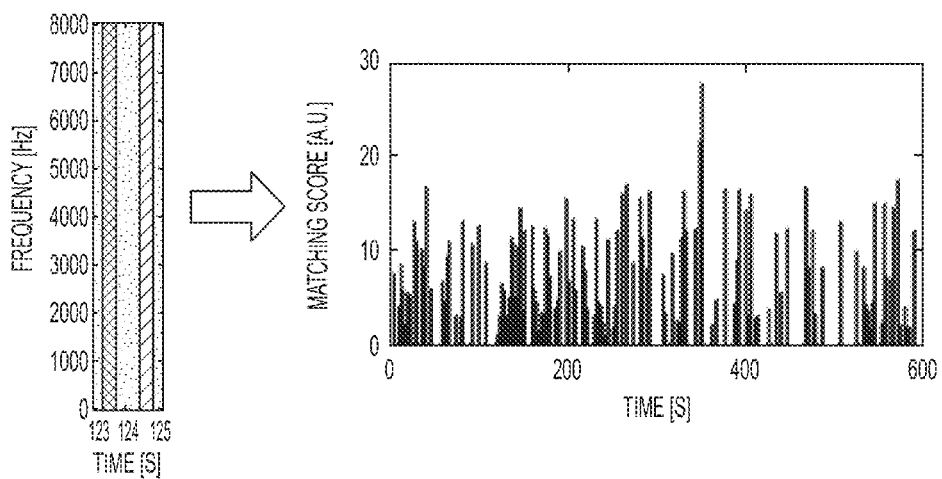
Figure 5C:
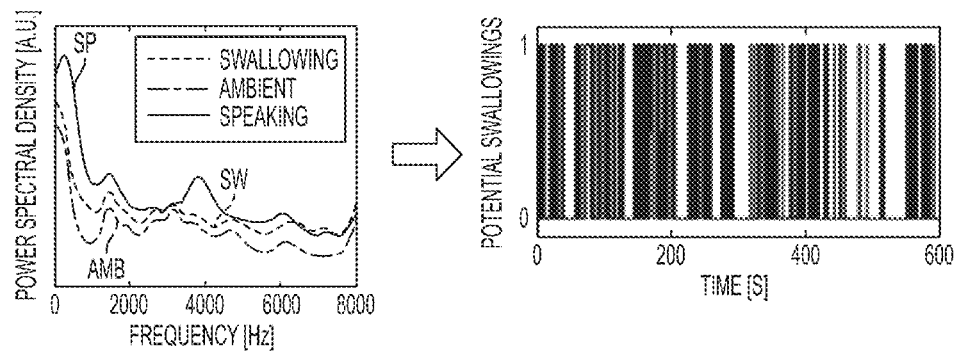
Figure 5D:
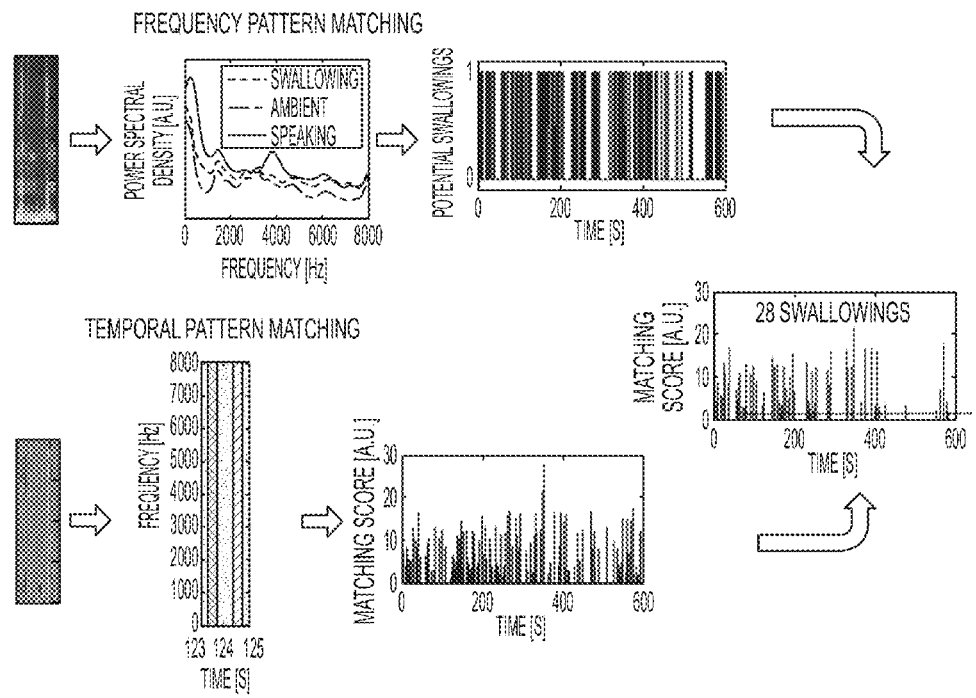

In some embodiments, swallowing events can be extracted using a combination of frequency and temporal pattern recognition. The processed spectrogram described above can be used to compute temporal gradient values. The correlation between the obtained temporal gradient values and a template characterized by consecutive positive, null, and negative gradient values can be computed over the entire recording. FIG. 5B illustrates an exemplary template and the resulting matching score for an exemplary sensor output. Speech episodes can be rejected by computing local power spectral densities (PSD) and testing for correlation with PSD templates of swallowing (SW), speaking (SP), and ambient (AMB) episodes, respectively, as shown in FIG. 5C. Template and binarized scores can be obtained by computing the template/processed spectrogram correlation for each sampling time. Maximum correlation values associated with the swallowing pattern can be scored as "1" while index values of "0" can be assigned otherwise. The frequency and temporal scores can then be multiplied to obtain a final index value. FIG. 5D schematically illustrates the complete processing scheme.

In other words, a first score can be obtained by performing frequency pattern matching and a second score can be obtained by performing temporal pattern matching. The product of the spectral score and the temporal score can be used as a detection threshold index. Microphone recordings with index values below the threshold amount can be excluded as not involving meal intake. Microphone recordings with index values greater than or equal to the threshold can be interpreted as meal intake by the user or, as discussed below, can be used in conjunction with other data to make such an interpretation. In some embodiments, the threshold index value for a throat or larynx microphone can be about 5.5. It will be appreciated that similar techniques can be used to obtain threshold values for microphones directed at other portions of the user, such as the user's stomach. Accordingly, a combination of frequency and temporal pattern matching can be used to detect swallowing events from the output of a throat microphone.

Electrocardiographs (ECG)

The one or more sensors can include an electrocardiograph ("ECG") configured to sense or detect electrical activity of the user's heart. The electrocardiograph can generate an output signal that represents the heart's electrical activity as a function of time. The electrocardiograph can include surface leads or electrodes configured for attachment to the user's skin and/or implantable leads or electrodes configured to be placed within the user's body. In some embodiments, the electrocardiograph can have a sampling rate of about 321.25 Hz. Exemplary electrocardiographs include the SEN3—Sense V2 System available from CSEM.

The electrocardiograph electrodes can be coupled to the user at a variety of locations. For example, as shown in FIG. 1, the electrocardiograph electrodes 116 can be coupled to the user's thorax or trunk at a plurality of locations. The electrocardiograph output can be used to determine the user's heart rate and to detect changes in the user's heart rate (e.g., heart rate variability (HRV)). The computer system 106 can analyze the electrocardiograph output and determine whether the HRV indicates an onset of the user ingesting food or drink.

Changes in heart rate can occur after ingestion, as discussed for example in Friesen et al., "Autonomic Nervous System Response To A Solid Meal And Water Loading In Healthy Children: Its Relation To Gastric Myoelectrical Activity," Neurogastroenterol Motil. 19(5): 376-382 (2007); Friesen et al., "The Effect Of A Meal And Water Loading On Heart Rate Variability In Children With Functional Dyspepia," Dig Dis Sci 55: 2283-2387 (2010); Yin et al., "Inhibitory Effects Of Stress On Postprandial Gastric Myoelectrical Activity And Vagal Tone In Healthy Subjects," Neurogastroenterol Motil 16(6): 737-744 (December 2004); Watanabe et al., "Effects of water ingestion on gastric electrical activity and heart rate variability in healthy subjects," J Auton Neuro Syst 58(1-2): 44-50 (1996); and Lipsitz et al., "Hemodynamic And Autonomic Nervous System Responses To Mixed Meal Ingestion In Healthy Young And Old Subjects And Dysautonomic Patients With Postprandial Hypotension," Circulation, 87: 391-400 (1993).

HRV analysis can be performed in a variety of ways, such as using time-domain and/or frequency-domain methods, as will be appreciated by a person skilled in the art. Generally, the time-domain methods can include calculations directly from raw R-R interval time series data, e.g., raw data of times from the peak of one R to the next R peak in a QRS complex of an echocardiogram, such as by using the standard deviation of all normal R-R intervals (SDNN), the standard deviation of the successive differences (SDSD) between R-R intervals, etc. Generally, the frequency-domain methods can include calculating a power spectral density (PSD) of R-R interval time series data. Calculating the PSD can be divided into nonparametric, e.g., fast Fourier transform (FFT) based calculations and parametric, e.g., autoregressive model, calculations. The PSD can be analyzed by calculating power and peak frequencies for different frequency bands, such as a very low frequency (VLF) band, e.g., in a range of about 0 to 0.04 Hz, a low frequency (LF) band, e.g., in a range of about 0.04 to 0.15 Hz, and a high frequency (HF) band, e.g., in a range of about 0.15 to 0.4 Hz. The LF band can represent sympathetic activity, and the HF band can represent parasympathetic activity.

In healthy, normal users after meal intake, power in the LF band can increase, while power in the HF band can decrease. Analysis of LF and HF bands can therefore result in a determination that meal intake has occurred when power in the LF band increases a certain threshold amount while power in the HF band decreases a threshold amount. Accordingly, in an exemplary embodiment, the computer system 106 can analyze a power spectral density in LF and HF bands to determine onset of meal intake. Such parameters are described in further detail in Lipsitz et al., "Hemodynamic And Autonomic Nervous System Responses To Mixed Meal Ingestion In Healthy Young And Old Subjects And Dysautonomic Patients With Postprandial Hypotension," Circulation, 87: 391-400 (1993) and in Lu et al., Digestive Diseases and Sciences, Vol 44 (4) 857-861.

Figure 6A:
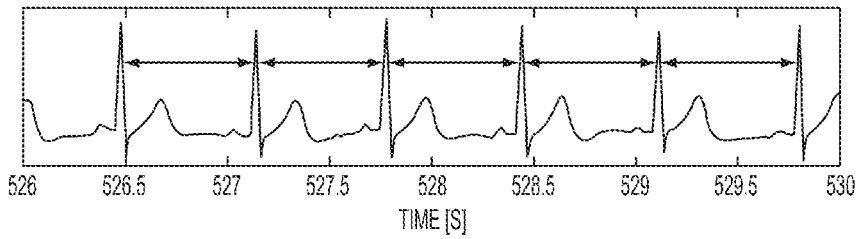
FIGS. 6A-6C illustrate an exemplary method of calculating an index for an electrocardiograph.

The electrocardiograph output can be received by the computer system 106 and can be conditioned and otherwise processed to detect meal intake by the user. FIG. 6A illustrates an exemplary raw output signal generated by the electrocardiograph and communicated to the computer system 106. The computer system 106 can analyze the sensor output in segments that correspond to discrete windows of time. For example, the computer system 106 can record the sensor output for a predetermined time period (e.g., 10 seconds, 30 seconds, 1 minute, 5 minutes, 10 minutes, etc.) and, at the conclusion of the predetermined time period or thereafter, analyze the sensor output corresponding to that time period.

The electrocardiograph output can be processed to identify R waves which represent heart beats. Interbeat intervals NN can then be extracted by the computer system 106 and various time-domain features can be extracted for a given time period (e.g., 5 minutes). Exemplary time-domain HRV features include the standard deviation of all NN intervals (SDNN), the square root of the mean of the squares of differences between adjacent NN intervals (RMSSD), and the standard deviation of differences between adjacent NN intervals (SDSD), each of which can be specified in milliseconds. A spectral analysis can then be performed using an autoregressive model to obtain various frequency-domain features. Exemplary frequency-domain features include the power in a very low frequency range (less than or equal to 0.04 Hz) (VLF), the power in a low frequency range (0.04 to 0.15 Hz) (LF), and the power in a high frequency range (0.15-0.4 Hz) (HF). The ratio of LF to HF can also be obtained (LF/HF). Any of these features can be used to determine whether the meal intake has occurred or is presently occurring.

Figure 6B:
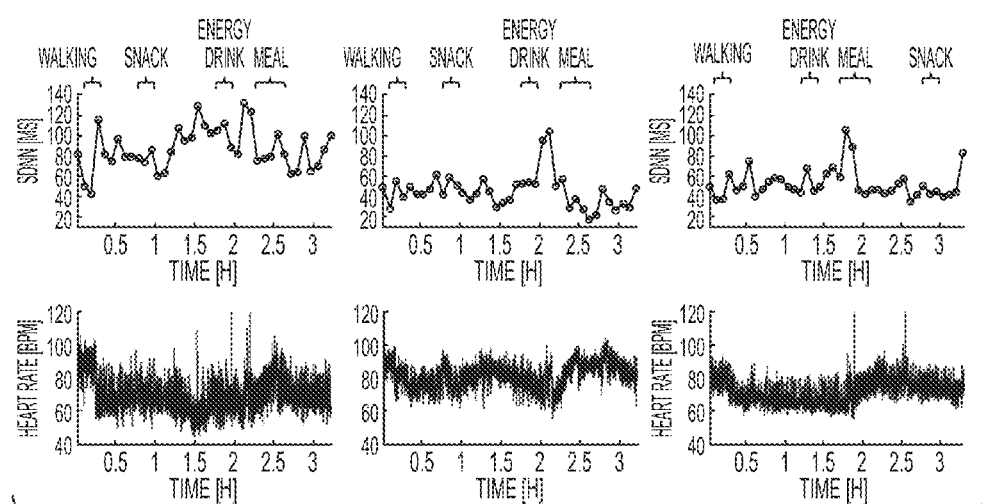
Figure 6C:
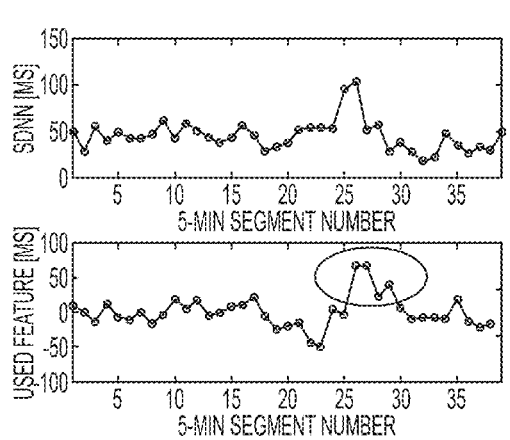

As shown in FIG. 6B, the SDNN parameter can decrease at the beginning of meal intake. Accordingly, SDNN can be used by the computer system 106 to calculate an index for use in a decision algorithm. For example, the negative of the moving average filtered value of the first derivative of the SDNN can be used. A decrease in SDNN produces a negative slope and thus a negative derivative. These values can be computed for each time segment, moving average filtered, and negated to be used by a decision algorithm in which a feature of interest should increase during meal intake episodes. FIG. 6C illustrates the obtained index, which is expected to be positive after meal intake episodes.

Time periods with index values below a threshold amount can be excluded as not involving meal intake. Time periods with index values greater than or equal to the threshold can be interpreted as meal intake by the user or, as discussed below, can be used in conjunction with other data to make such an interpretation. In some embodiments, the threshold amount can be about −3.8. Accordingly, a negative slope based index can be used by the computer system 106 to determine from the electrocardiograph output whether digestion is occurring.

Temperature Sensors

The one or more sensors can include a temperature sensor configured to measure the user's body temperature. In particular, the user's skin temperature can be measured at one or more locations using temperature sensors. The temperature sensors can generate an output signal that represents the user's temperature as a function of time. In some embodiments, the temperature sensors can have a sampling rate of about 0.2 Hz. Exemplary temperature sensors include the SEN Orange-Sensi Medi System available from CSEM.

The temperature sensor(s) can be coupled to the user at a variety of locations. For example, as shown in FIG. 1, temperature sensors 118 can be coupled to the user's thorax or trunk at a plurality of locations. The temperature sensors can also be coupled to the user's ear lobes. The temperature sensor output can be used to determine the user's temperature and changes in the user's temperature. When a plurality of temperature sensors are used, a temperature gradient of the user can be measured. Thus, in some embodiments, a plurality of temperature sensors can be coupled to the user's torso to detect the temperature gradient across the user's torso.

Figure 7A:
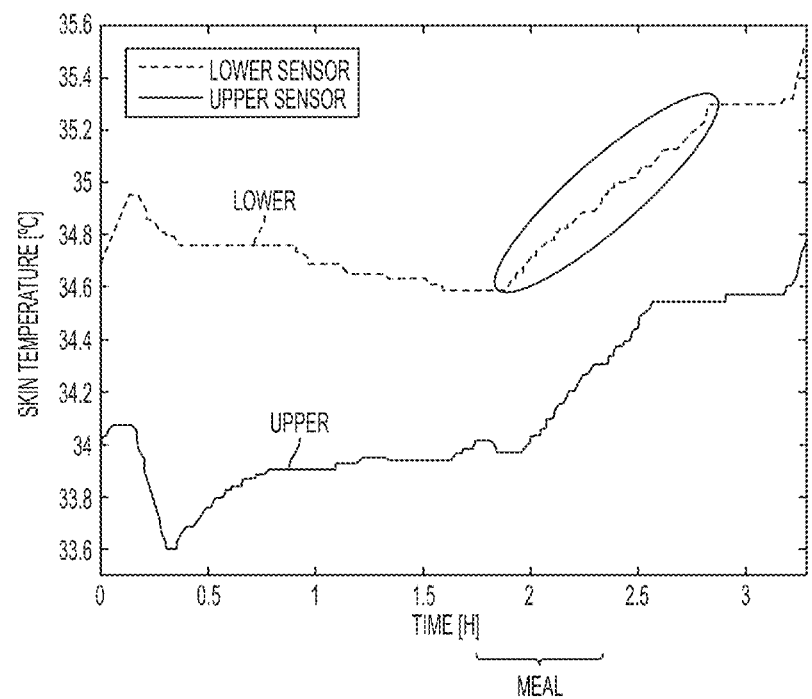
FIGS. 7A-7E illustrate an exemplary method of calculating an index for a temperature sensor.

The temperature sensor output can be received by the computer system 106 and can be conditioned and otherwise processed to detect ingestion by the user. For example, increases in user temperature can be associated with meal intake. FIG. 7A illustrates exemplary raw output signals generated by upper torso and lower torso temperature sensors and communicated to the computer system 106. The illustrated time period shows the output before, during, and after a meal is consumed by the user. As shown, the user's skin temperature generally increases during and after meal ingestion. The computer system 106 can analyze the sensor output in segments that correspond to discrete windows of time. For example, the computer system 106 can record the sensor output for a predetermined time period (e.g., 10 seconds, 30 seconds, 1 minute, 5 minutes, 10 minutes, etc.) and, at the conclusion of the predetermined time period or thereafter, analyze the sensor output corresponding to that time period.

Figure 7B:
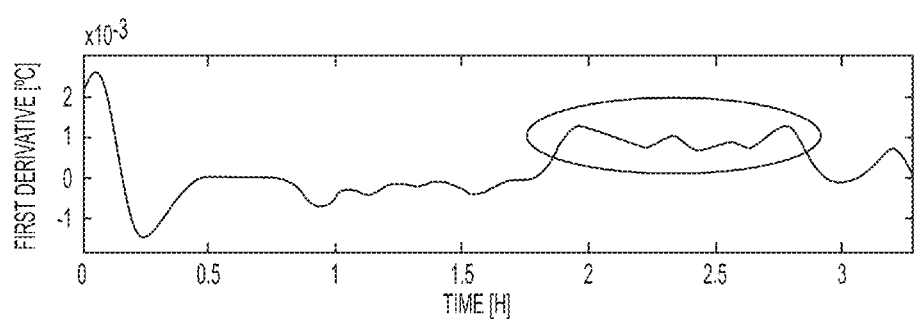
Figure 7C:
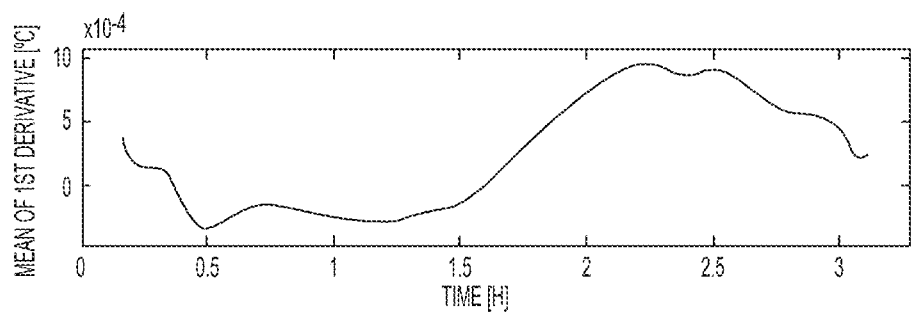
Figure 7D:
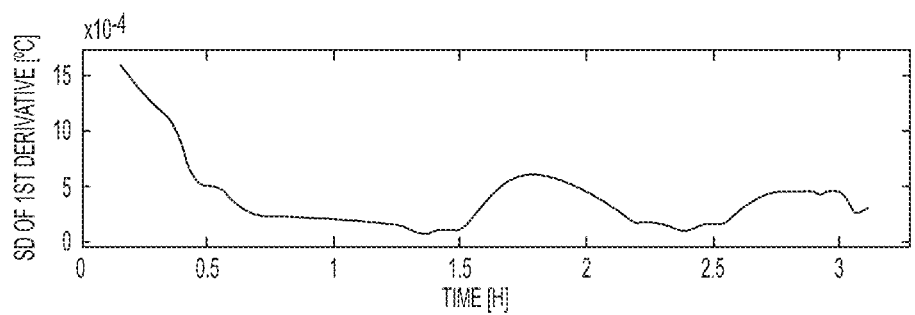
Figure 7E:
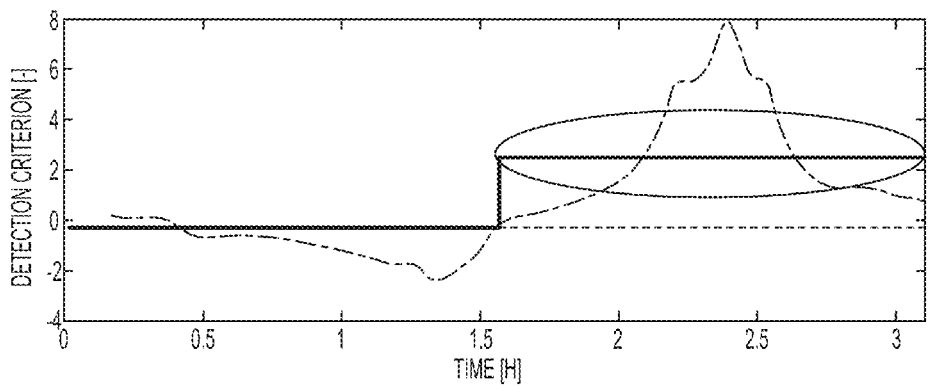

In some embodiments, a positive slope based index can be used to evaluate the temperature sensor output. The computer system 106 can compute the first derivative of the lower torso skin temperature, as shown in FIG. 7B. A low-pass finite-impulse-response (FIR) filter can then be applied to the first derivative using a simple moving average window which can be, e.g., 30 minutes in length to extract the low frequency components of the first derivative signal, as shown in FIG. 7C. The standard deviation of the lower torso skin temperature can then be computed and the same FIR filter can be applied to the resulting signal, as shown in FIG. 7D. The computer system's decision algorithm can use a temperature index calculated as the ratio of the low frequency components of the first derivative signal to the low frequency components of the standard deviation values. Exemplary index values as a function of time are shown in FIG. 7E. As shown, the temperature index can be positive after meal intake episodes. Time periods with index values below a threshold amount can be excluded as not involving meal intake. Time periods with index values greater than or equal to the threshold can be interpreted as meal intake by the user or, as discussed below, can be used in conjunction with other data to make such an interpretation. In some embodiments, the threshold amount can be about −0.35. Accordingly, a positive slope based index can be used to determine from the temperature sensor data whether digestion is occurring.

Accelerometers

The one or more sensors can include an accelerometer configured to sense or detect movement of one or more portions of the user. The accelerometer can generate an output signal that represents the user's movements as a function of time. In some embodiments, the accelerometer can have a sampling rate of about 30 Hz. Exemplary accelerometers include the GT3+ monitor 3D accelerometer available from Actigraph, LLC.

The accelerometer can be coupled to, or configured to measure, movement of various portions of the user. For example, as shown in FIG. 1, 3D-axis accelerometers 120 can be embedded into devices worn at the wrist, e.g., such that a first accelerometer is coupled to the user's left wrist and a second accelerometer is coupled to the user's right wrist. In other embodiments, a single accelerometer can be used. Accelerometers can also be coupled to other portions of the user, such as the user's jaw or throat.

The accelerometer output can be received by the computer system 106 and can be conditioned and otherwise processed to detect meal intake by the user. The computer system 106 can analyze the sensor output in segments that correspond to discrete windows of time. For example, the computer system 106 can record the sensor output for a predetermined time period (e.g., 10 seconds, 30 seconds, 1 minute, 5 minutes, 10 minutes, etc.) and, at the conclusion of the predetermined time period or thereafter, analyze the sensor output corresponding to that time period.

Figure 8A:
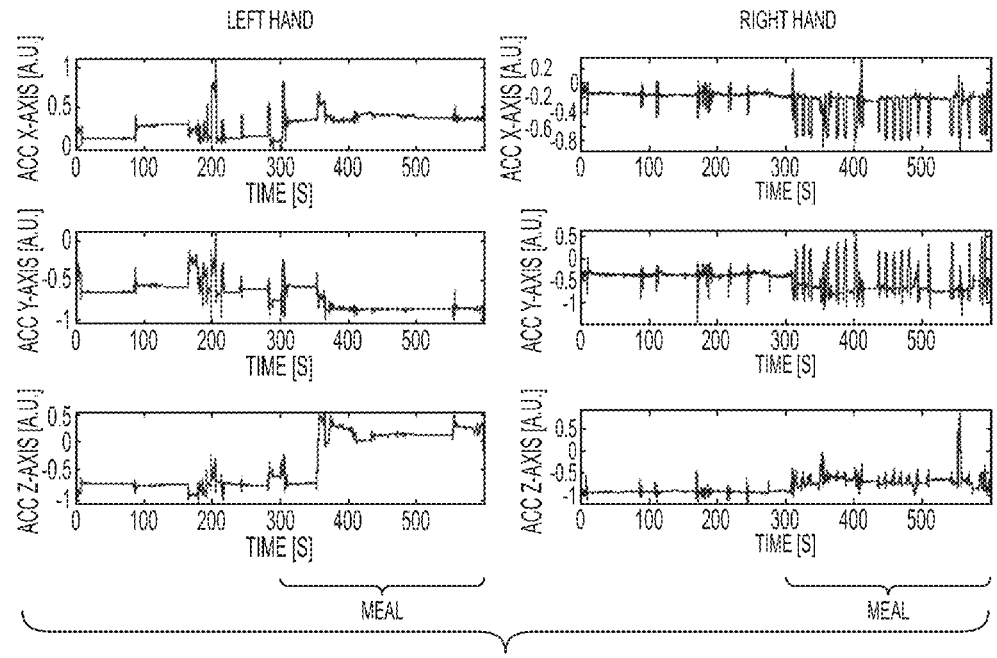
FIGS. 8A-8E illustrate an exemplary method of calculating an index for an accelerometer.
Figure 8B:
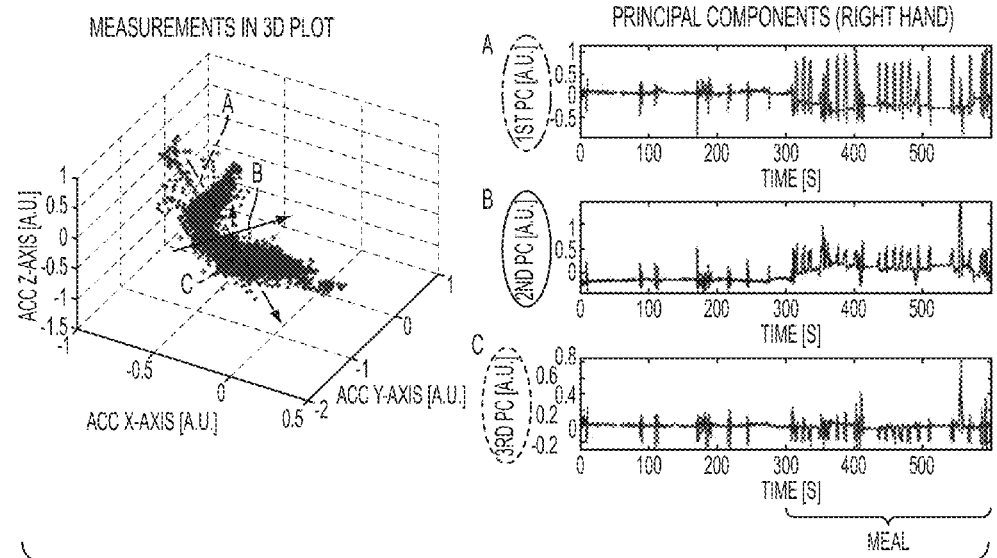
Figure 8C:
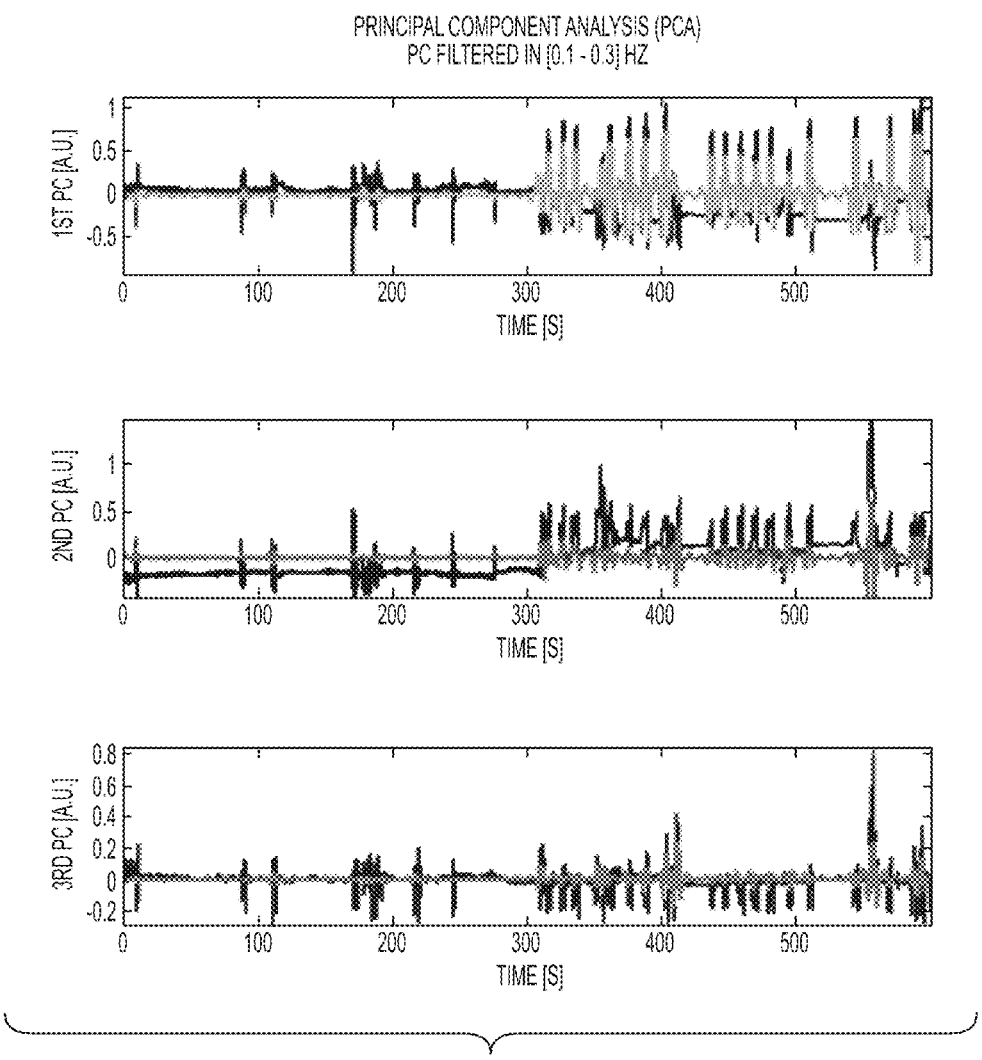
Figure 8D:
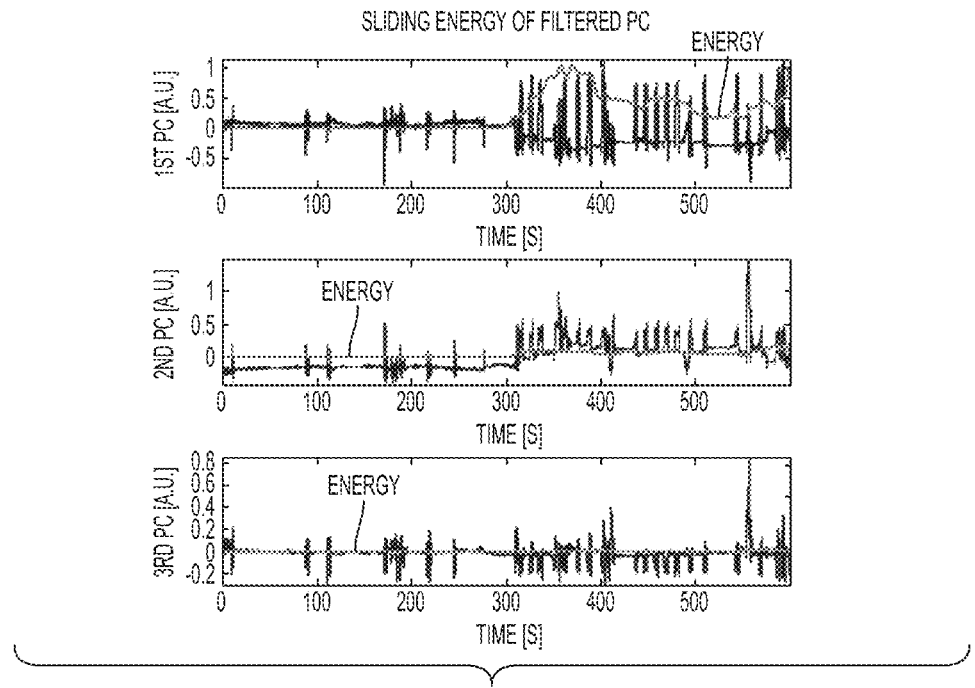
Figure 8E:
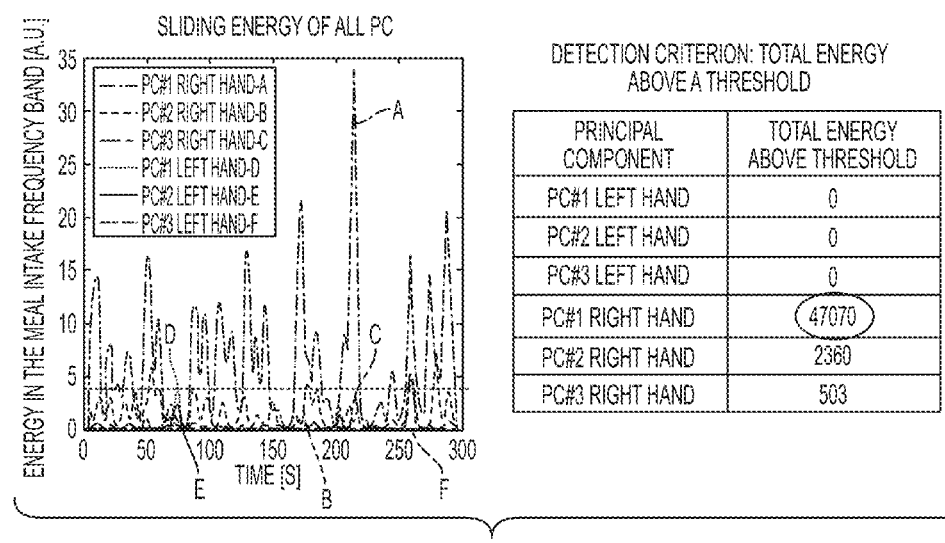

FIG. 8A illustrates an exemplary raw output signal generated by the accelerometers and communicated to the computer system 106. The illustrated signals include a time period during which meal ingestion occurred and, as shown, a discernable pattern of motion occurs during meal intake. The 3D information contained in the accelerometer output is shown in FIG. 8B. A principal component analysis (PCA) can be used to project the 3D-axis components into orthogonal bases with minimal correlation, as also shown in FIG. 8B. The PCA components can be used to extract the motion pattern by applying a band-pass FIR filter (e.g., 0.1-0.3 Hz) to the PCA components, as shown in FIG. 8C. The energy of these filtered signals can then be computed as shown in FIG. 8D and, from that information, the total energy above a heuristically-defined threshold (e.g., about 4.0) can be computed to produce an index for the computer system's decision algorithm, as shown in FIG. 8E.

Time periods with index values below a threshold index amount can be excluded as not involving meal intake. Time periods with index values greater than or equal to the threshold can be interpreted as meal intake by the user or, as discussed below, can be used in conjunction with other data to make such an interpretation. In some embodiments, the threshold amount can be about 13,767. Accordingly, energy in a frequency band of interest can be used as an index to determine from the accelerometer output when meal intake activities are occurring.

Electrogastrographs (EGG)

The one or more sensors can include an electrogastrograph ("EGG") or an electrogastroenterograph configured to sense or detect electrical activity of the user's gastrointestinal system (e.g., stomach, small intestine, colon, and so forth). The electrogastrograph can generate an output signal that represents electrical activity as a function of time. The electrogastrograph can include surface leads or electrodes configured for attachment to the user's skin and/or implantable leads or electrodes configured to be placed within the user. In some embodiments, the electrogastrograph can have a sampling rate of about 312.5 Hz. Exemplary electrogastrographs include the Biopac MP150 Data Acquisition System and the Biopac EGG100C available from Biopac Systems, Inc.

The electrogastrograph electrodes can be coupled to, or configured to measure, various portions of the user. For example, as shown in FIG. 1, the electrogastrograph electrodes 122 can be coupled to various places on the user's abdomen.

The electrogastrograph output can be received by the computer system 106 and can be conditioned and otherwise processed to detect meal intake by the user. The computer system 106 can analyze the sensor output in segments that correspond to discrete windows of time. For example, the computer system 106 can record the sensor output for a predetermined time period (e.g., 10 seconds, 30 seconds, 1 minute, 5 minutes, 10 minutes, etc.) and, at the conclusion of the predetermined time period or thereafter, analyze the sensor output corresponding to that time period.

Figure 9A:
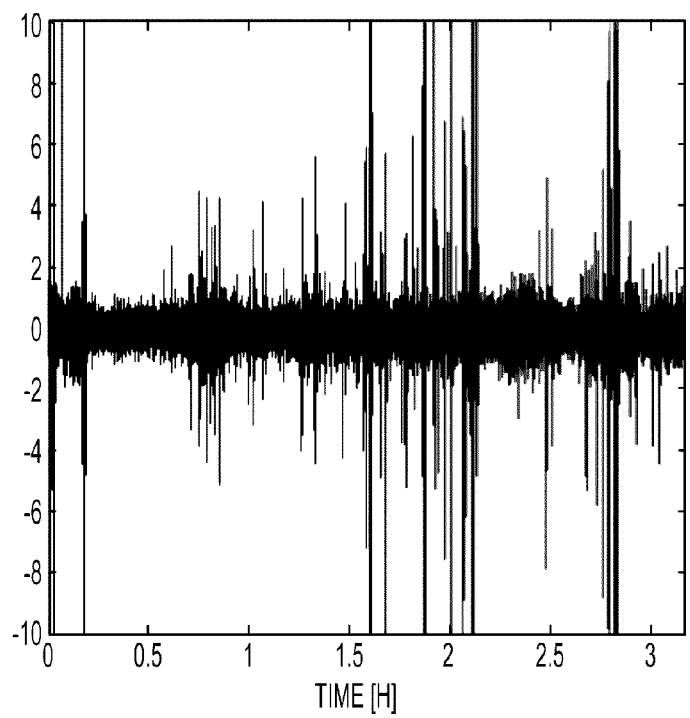
FIGS. 9A-9C illustrate an exemplary method of calculating an index for an electrogastrograph.
Figure 9B:
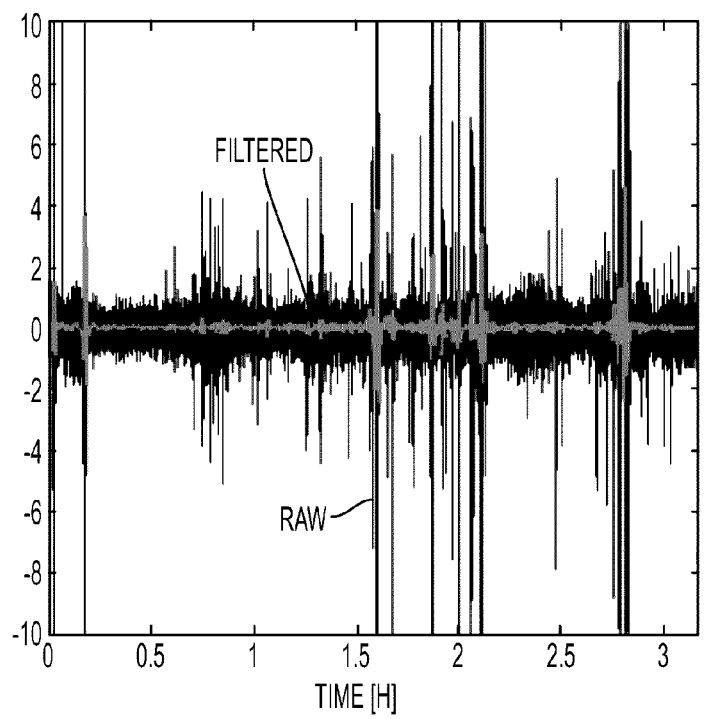
Figure 9C:
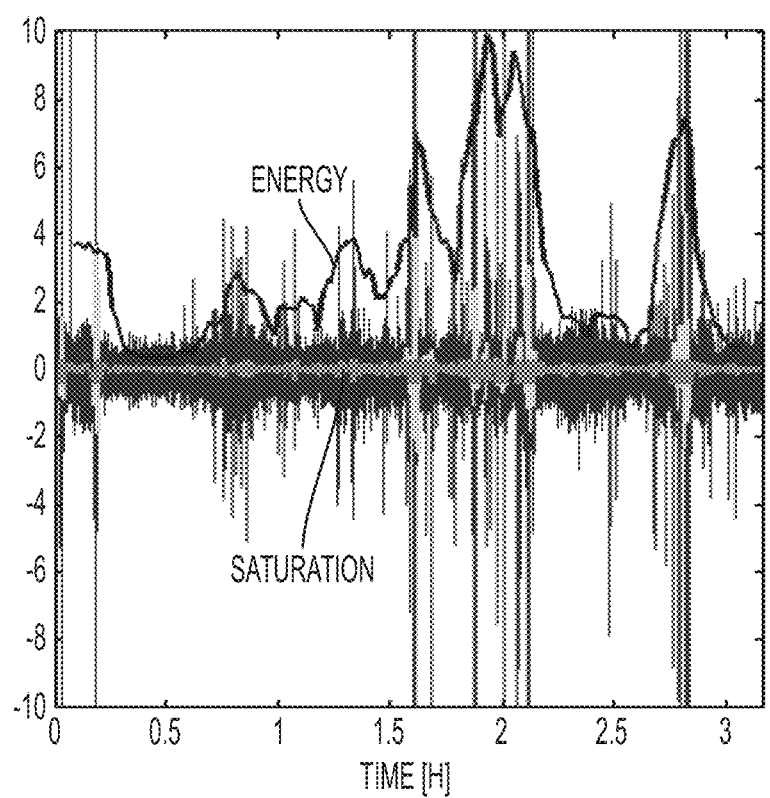

FIG. 9A illustrates an exemplary raw output signal generated by the electrogastrograph and communicated to the computer system 106. In some embodiments, the local energy of the electrogastrograph output filtered in a frequency zone of interest can be used as an index for the computer system's decision algorithm. The computer system 106 can filter the EGG output in the frequency domain of the intestine (e.g., 0.01-0.03 Hz), as shown in FIG. 9B. A saturation can be applied on the filtered signal to reduce motion-induced artifacts, as shown in FIG. 9C. The sliding energy of the cropped-filtered signals can then be computed and the total energy can be used as an index.

Time periods with index values below a threshold amount can be excluded as not involving meal intake. Time periods with index values greater than or equal to the threshold can be interpreted as meal intake by the user or, as discussed below, can be used in conjunction with other data to make such an interpretation. In some embodiments, the threshold amount can be about 0.015. Accordingly, an amplitude-based index can be used to determine from the electrogastrograph output whether digestion is occurring.

Impedance Sensors

The one or more sensors can include an impedance sensor configured to sense or measure the impedance across one or more portions of the user's body. The impedance sensor can generate an output signal that represents the impedance as a function of time. The impedance sensor can include surface leads or electrodes configured for attachment to the user's skin and/or implantable leads or electrodes configured to be placed within the observed portion of the user, e.g., in the form of needles or wires. In some embodiments, the impedance sensor can have a sampling rate of about 312.5 Hz. Exemplary impedance sensors include the Biopac MP150 Data Acquisition System and the Biopac EBI100C available from Biopac Systems, Inc.

Figure 10A:
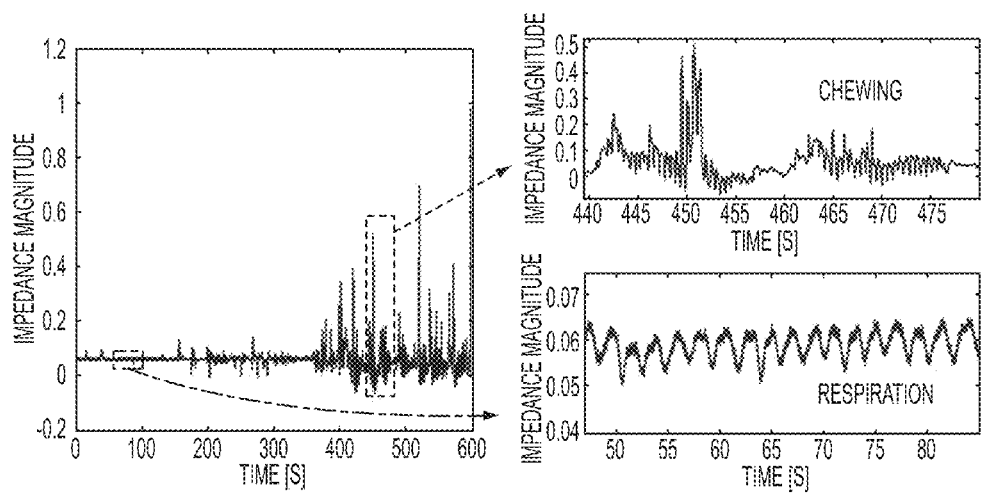
FIGS. 10A-10B illustrate an exemplary method of calculating an index for an impedance sensor.

The impedance sensor electrodes can be coupled to, or configured to measure, various portions of the user. For example, as shown in FIG. 1, the impedance sensor electrodes 124 can be coupled to the user's neck. Each time a bolus of ingested solids or liquids passes through the user's neck, a change in impedance can be observed. As shown in FIG. 10A, respiration and chewing artifacts can also be observed in the impedance sensor output.

The impedance sensor output can be received by the computer system 106 and can be conditioned and otherwise processed to detect meal intake by the user. The computer system 106 can analyze the sensor output in segments that correspond to discrete windows of time. For example, the computer system 106 can record the sensor output for a predetermined time period (e.g., 10 seconds, 30 seconds, 1 minute, 5 minutes, 10 minutes, etc.) and, at the conclusion of the predetermined time period or thereafter, analyze the sensor output corresponding to that time period.

Figure 10B:
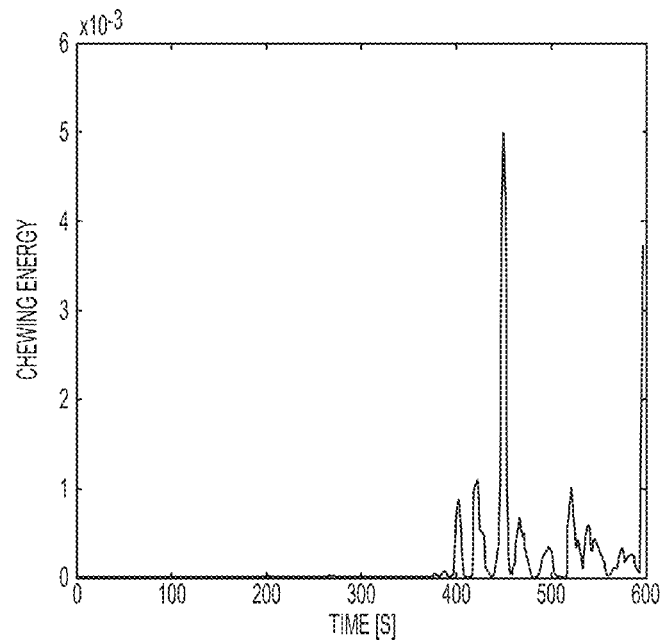

FIG. 10A illustrates an exemplary raw output signal generated by the impedance sensor, with inset portions showing the output during chewing and during respiration. The output signal can be communicated to the computer system 106, which can use an energy-based index to determine when ingestion is occurring. The computer system 106 can apply a band-pass FIR filter on the impedance-measurement signals. The chewing band can be fixed between, e.g., 1.5 to 2.5 Hz. The median energy in the frequency range of interest can be used as an index for the computer system's decision algorithm. The estimated energy as a function of time is shown in FIG. 10B, in which meal intake began at T=360 s. As shown, estimated energy peaks coincide with meal intake.

Time periods with index values below a threshold amount can be excluded as not involving meal intake. Time periods with index values greater than or equal to the threshold can be interpreted as meal intake by the user or, as discussed below, can be used in conjunction with other data to make such an interpretation. In some embodiments, the threshold amount can be about $1.4 \times 10^{-5}$. Accordingly, an energy-based index can be used to determine from the impedance sensor output when chewing occurs.

Impedance of other portions of the user's body can also be sensed including, for example, the impedance across the user's stomach wall. Sensing and processing gastric impedance data and/or using changes in gastric impedance to detect eating is described in more detail in U.S. Pat. Pub. No. 2009/0192404 filed Jan. 28, 2008 entitled "Methods And Devices For Measuring Impedance In A Gastric Restriction System," Silny et al, "Verification of the intraluminal multiple electrical impedance measurement for the recording of gastrointestinal motility," Neurogastroenterology & Motility, Vol 5(2): 107-122 (June 1993); and "Effects of Thickened Feeding on Gastroesophageal Reflux in Infants: A Placebo-Controlled Crossover Study Using Intraluminal Impedance," Pediatrics 111(4), e355-e359 (April 2003).

FIGS. 11A-11F illustrate various exemplary patterns in which the impedance sensor electrodes can be coupled to the user.

Figure 11A:
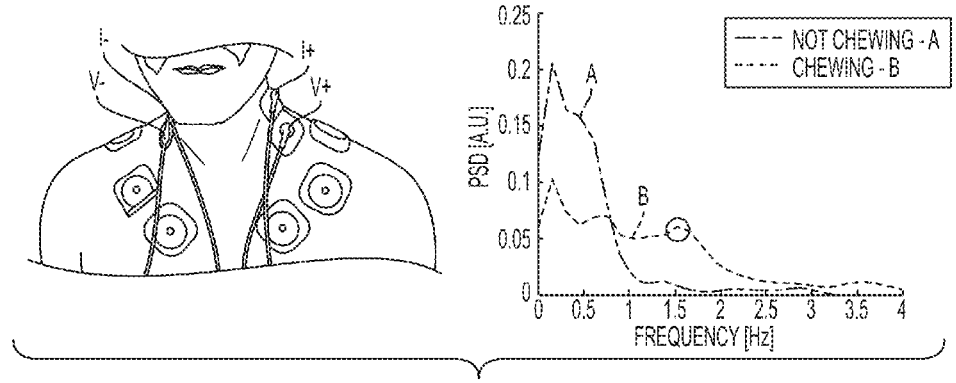
FIGS. 11A-11F illustrate exemplary placements of impedance sensor electrodes on a patient.

In FIG. 11A, the I– and I+ electrodes are coupled to opposite sides of the user's throat, just beneath the jaw. The V– and V+ electrodes are coupled to opposite sides of the user's neck, at the base of the neck, just above the clavicle and in front of the trapezius.

Figure 11B:
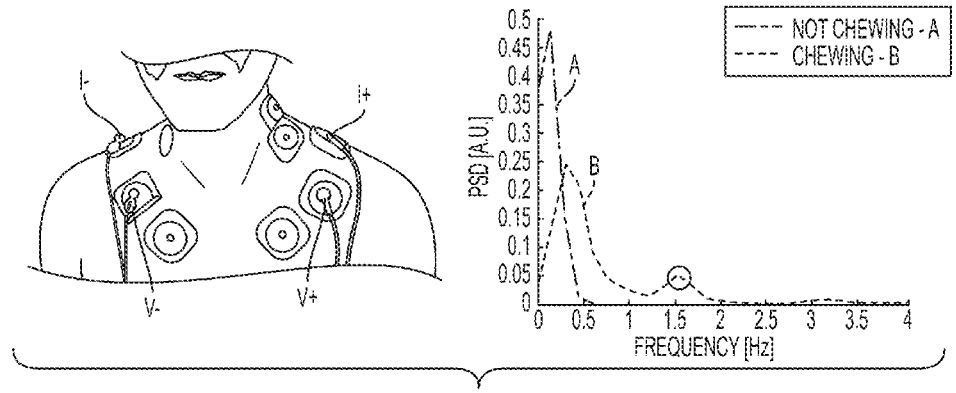

In FIG. 11B, the I– and I+ electrodes are coupled to the user's right and left trapezius muscles, respectively, about half way between the user's neck and shoulder. The V– and V+ electrodes are coupled to opposite sides of the user's chest, just below the clavicle and about half way between the user's neck and shoulder.

Figure 11C:
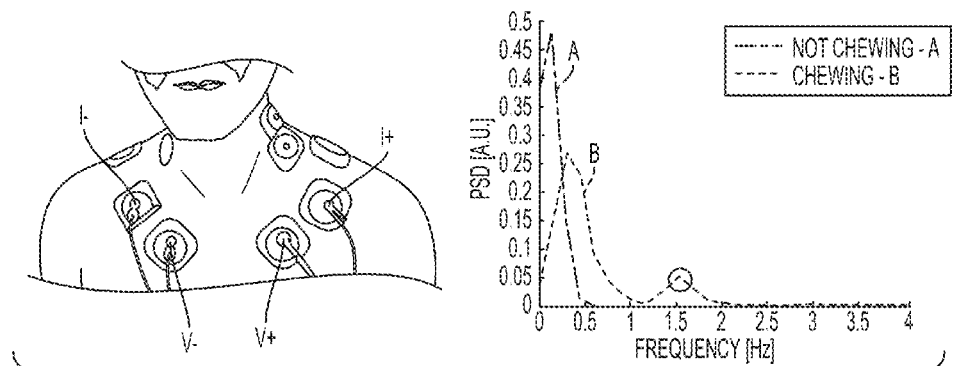

In FIG. 11C, the I– and I+ electrodes are coupled to opposite sides of the user's chest, just below the clavicle and about half way between the user's neck and shoulder. The V– and V+ electrodes are coupled to opposite sides of the user's chest, just beneath the I– and I+ electrodes and inward towards the sternum.

Figure 11D:
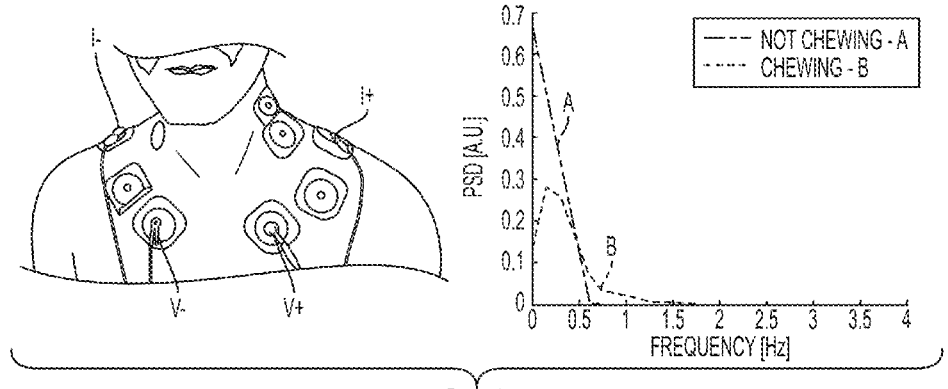

In FIG. 11D, the I– and I+ electrodes are coupled to the user's right and left trapezius muscles, respectively, about half way between the user's neck and shoulder. The V– and V+ electrodes are coupled to opposite sides of the user's chest, beneath the clavicle and closer to the sternum than to the shoulder.

Figure 11E:
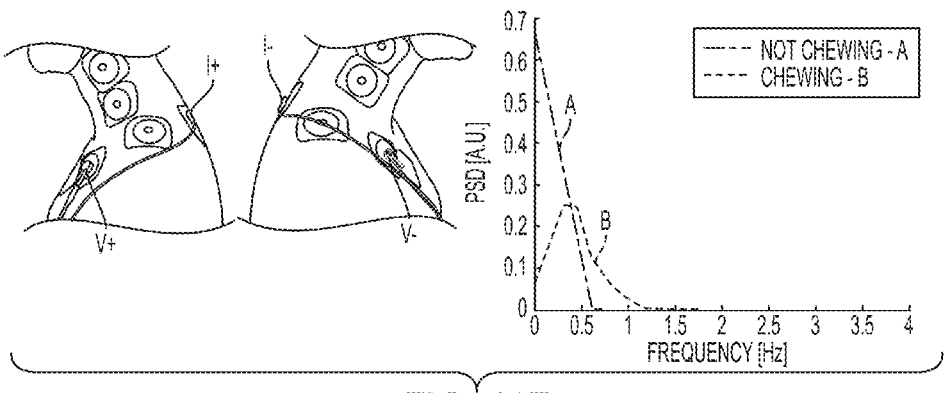

In FIG. 11E, the I– and I+ electrodes are coupled to opposite sides of the user's back, just below the base of the neck. The V– and V+ electrodes are coupled to opposite sides of the user's chest, just below the clavicle and about half way between the user's neck and shoulder.

Figure 11F:
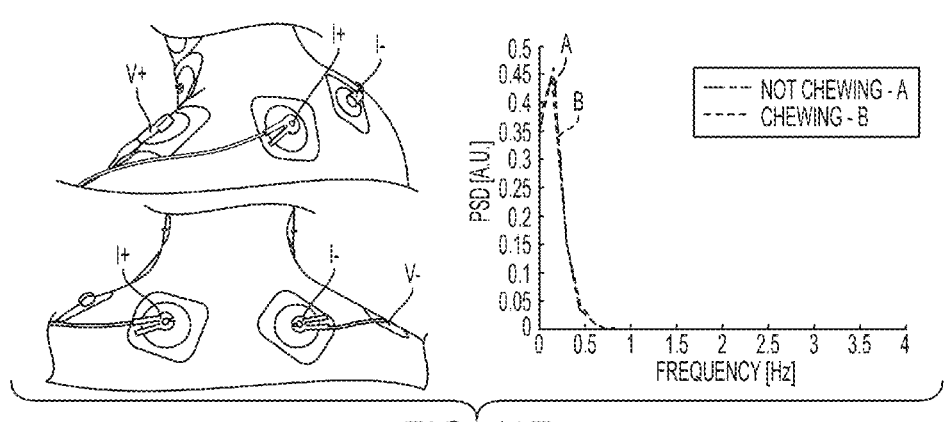

In FIG. 11F, the I– and I+ electrodes are coupled to opposite sides of the user's back, just below the base of the neck. The V– and V+ electrodes are coupled to the user's right and left trapezius muscles, respectively, about half way between the user's neck and shoulder.

The output graphs that accompany each electrode placement diagram illustrate exemplary impedance power spectral density (PSD) as detected by the impedance sensor during chewing and non-chewing episodes. As shown, the electrode placement of FIGS. 11A-11C can provide a PSD of about 0.05 at 1.5 Hz during chewing episodes, which can be readily distinguished from non-chewing episodes. The electrode placement of FIGS. 11D-11F can result in less of a distinction in the sensor output between chewing and non-chewing episodes. While the electrode placement of FIG. 11A can provide the strongest response to chewing episodes, the electrode placement of FIGS. 11B-11C can be preferred in some embodiments, as these placements can be easily hidden under the user's clothing and also provide a strong response to chewing episodes. It will be appreciated that a variety of other electrode placements can be used in addition to those specifically illustrated and described herein.

Heart Rate Sensors

While ECG sensors are disclosed above for detecting the user's heart rate, it will be appreciated that other heart rate sensors can be used instead or in addition. Heart rate sensors can be configured to gather heart rate data for the user, including changes in heart rate, e.g., HRV. Heart rate sensors can be subcutaneously positioned or implanted within the user, e.g., at the distal esophagus, the proximal stomach, or the mid/distal stomach. Heart rate sensors can also be transcutaneously positioned or positioned external to the user such as positioned on an external skin surface thereof. One or more heart rate sensors can be disposed at a variety of locations around the user, e.g., the wrist and the sternum, and each of the heart rate sensors can be configured to communicate sensed data to the computer system 106.

Externally-located heart rate sensors can include a strap configured to be worn by the user such that a heart rate sensing electrode attached to the strap is positioned on an exterior skin surface of a chest of the user, a heart rate sensing electrode attached to an article of clothing configured to be worn by the user such that the electrode contacts an exterior skin surface of the user, and a pulse oximeter configured to be positioned on an external skin surface of a finger of a user. Exemplary embodiments of a heart rate sensor configured to be positioned within the user include a lead configured to be implanted within a heart of the user, and an electrode configured to be implanted on a thorax of the user.

pH Sensors

The one or more sensors can include a pH sensor configured to gather digestive tract pH levels of the user, e.g., pH levels within the user's stomach. A pH sensor can be implanted in the user, such as within a gastrointestinal tract of the user, e.g., within the user's stomach, within the user's intestine, within the user's mouth (e.g., a dental implant), etc.

Variations in gastric pH can indicate whether or not there is solid food present in the stomach. The relationship between gastric pH levels and food consumption is described in further detail in "Regional Postprandial Differences in pH Within the Stomach and Gastroesophageal Junction," Digestive Diseases and Sciences, Vol. 50, No. 12 (December 2005), pgs. 2276-2285. Using intraluminal pH sensors to detect eating is described in more detail in "Effects of Thickened Feeding on Gastroesophageal Reflux in Infants: A Placebo-Controlled Crossover Study Using Intraluminal Impedance," Pediatrics 111(4), e355-e359 (April 2003). In general, gastric pH is low in an empty stomach. Upon eating, especially foods that contain protein, gastric pH can become more basic (i.e., the pH value increases) due to buffering by the food. The increase in pH can occur even though the stomach is actively secreting acid. Once the buffering capacity of the food is exceeded, the gastric pH can return to a low value. Thus, as described in further detail in U.S. Pat. Pub. No. 2009/0192534 filed Jan. 29, 2008 entitled "Sensor Trigger" and in "Regional Postprandial Differences in pH Within the Stomach and Gastroesophageal Junction," Diseases and Sciences, Vol. 50, No. 12 (December 2005), the gastric pH level can increase after each meal and return to the baseline pH sometime thereafter.

The pH sensor can be configured to communicate the sensed data to the computer system 106. The computer system 106 can in turn be configured to determine whether a change in gastric pH of a selected magnitude occurred, e.g., |X-Y| pH, or whether the pH rises above a threshold value, e.g., above about 7. Time periods in which the pH exceeds the threshold or in which pH changes of a selected magnitude occur can be interpreted as meal intake by the user or, as discussed below, can be used in conjunction with other data to make such an interpretation. Accordingly, gastric pH sensors can be used to determine when digestion occurs.

Gastric Stretch Sensors

In some embodiments, the one or more sensors can include a gastric stretch sensor, e.g., a strain gauge and strap disposed around the user's abdomen. Various embodiments of collecting and/or analyzing gastric stretch data to determine when eating occurs are described in more detail in Paintal, et al., "A Study Of Gastric Stretch Receptors: Their Role In The Peripheral Mechanisms Of Satiation Of Hunger And Thirst," Journal of Physiology, Vol. 126, 255-270 (1954), and Geliebter et al., "Gastric Distension By Balloon And Test-Meal Intake In Obese And Lean Subjects," Am J Clin Nutr, Vol 48, 592-594 (1988).

Combinations of Sensors

As noted above, the computer system 106 can be configured to make a meal intake determination based on the output of a single sensor or based on the output of a plurality of sensors. A number of exemplary sensor combinations are discussed below, however it will be appreciated that virtually any combination of the sensors described herein can be used.

As shown in FIG. 12, the EMG and impedance sensors can have high sensitivity and high specificity when distinguishing between solid food intake and other activities such as drinking, resting, and exercising. The accelerometer and microphone sensors can have high sensitivity and high selectivity when distinguishing between solid or liquid food intake and other activities such as resting and exercising. The temperature, HRV, and EGG sensors can have relatively lower sensitivity and/or specificity when determining when digestion is occurring.

In some embodiments, the one or more sensors can include an EMG sensor and an accelerometer, and can be effective to detect solid and liquid food intake with high specificity and high sensitivity. For example, the computer system 106 can be configured to detect that solid food intake occurs when the EMG sensor exceeds the index threshold. The computer system 106 can be configured to detect that drinking occurs when the EMG sensor is below the index threshold and the accelerometer is above the index threshold. When neither sensor is above the index threshold, the computer system 106 can determine that no solid food intake or drinking is occurring.

In some embodiments, the one or more sensors can include an impedance sensor and an accelerometer, and can be effective to detect solid and liquid food intake with high specificity and high sensitivity. For example, the computer system 106 can be configured to detect that solid food intake occurs when the impedance sensor exceeds the index threshold. The computer system 106 can be configured to detect that drinking occurs when the impedance sensor is below the index threshold and the accelerometer is above the index threshold. When neither sensor is above the index threshold, the computer system 106 can determine that no solid food intake or drinking is occurring.

In some embodiments, the one or more sensors can include an EMG sensor and a microphone, and can be effective to detect solid and liquid food intake with high specificity and high sensitivity. For example, the computer system 106 can be configured to detect that solid food intake occurs when the EMG sensor exceeds the index threshold. The computer system 106 can be configured to detect that drinking occurs when the EMG sensor is below the index threshold and the microphone is above the index threshold. When neither sensor is above the index threshold, the computer system 106 can determine that no solid food intake or drinking is occurring.

In some embodiments, the one or more sensors can include an impedance sensor and a microphone, and can be effective to detect solid and liquid food intake with high specificity and high sensitivity. For example, the computer system 106 can be configured to detect that solid food intake occurs when the impedance sensor exceeds the index threshold and the microphone exceeds the index threshold. The computer system 106 can be configured to detect that drinking occurs when the impedance sensor is below the index threshold and the microphone is above the index threshold. When neither sensor is above the index threshold, the computer system 106 can determine that no solid food intake or drinking is occurring.

As shown in FIG. 13, sensor combinations can advantageously allow solid food intake and drinking to be distinguished from other activities such as resting and exercising with high sensitivity and specificity.

Controlled Devices

As noted above, a controlled device 108 can be coupled to the meal detection system 100 such that the meal detection system is configured to trigger, modulate, or otherwise control the controlled device 108 based on determinations made by the computer system 106. In particular, when the computer system 106 determines that meal intake has occurred or is presently occurring, it can trigger, modulate, or otherwise control one or more controlled devices 108.

The computer system 106 can be configured to transmit a trigger signal to the controlled device 108. The trigger signal can have a variety of configurations, such as a simple on/off signal configured to change the controlled device 108 from a dormant or off mode, in which the controlled device 108 does not deliver therapy or record that meal intake has occurred, to a delivery or on mode in which the controlled device 108 delivers a therapy to the user or records that meal intake has occurred. The trigger signal can trigger a timer at the controlled device 108 that can initiate delivery of a therapy after a predetermined period of time has passed, e.g., 15 minutes, etc., such that the therapy can be initiated a certain amount of time after the detection of a meal has occurred. The trigger signal can optionally include data related to the meal ingested by the user, e.g., an amount or estimated amount of food eaten. The controlled device 108 can be configured to record this data for subsequent analysis or reporting. Alternatively or in addition, the controlled device 108 can be configured to use such data to determine an amount of therapy to deliver to the user, e.g., a certain volume of chemical to be delivered thereto, and/or a length of time to deliver the therapy to the user. The computer system 106 can be configured to include with the trigger signal instructions regarding the amount of the therapy to deliver to the user and/or the length of time to deliver the therapy to the user. In some embodiments, after transmitting the trigger signal to the controlled device 108, the computer system 106 can be configured to transmit a second, subsequent trigger signal to the controlled device 108 to cause the device to stop delivering the therapy to the user. The second, subsequent trigger signal can be sent for any number of reasons, such as after a certain period of time or if, based on sensed data gathered by the at least one sensor 104, the computer system 106 determines that the user has ceased meal intake.

Upon receipt of the trigger signal, the controlled device 108 can be configured to deliver a therapy to the user for any length of time. In some embodiments, the trigger signal can be configured to trigger delivery of the therapy for an indefinite period of time. In other words, the controlled device 108 can be configured to have a default off mode in which the device does not deliver the therapy to the user, and be configured to permanently switch to an on mode during which the device 108 delivers the therapy to the user. The indefinite period of time can be established by an amount of the therapy available to the device 108, e.g., if the device 108 includes a finite supply of a chemical therapy, can be defined by an amount of power available to the device 108, e.g., battery life, and/or can be defined by a likely-unknown period of time before a predetermined termination event occurs that triggers an end of the therapy's delivery to the user. The predetermined termination event can include, e.g., an end of a meal intake episode as determined by the computer system 106 and communicated from the computer system to the controlled device 108. In other embodiments, the trigger signal can be configured to trigger delivery of the therapy for a predetermined time period, e.g., a period of "N" seconds, minutes, etc. in which the device 108 is configured to deliver the therapy to the user before stopping delivery thereof if and until the computer system 106 communicates another trigger signal to the device 108 to again start delivery of the therapy.

The device 108 can therefore be configured to intermittently deliver the therapy to the user. In other words, the device can be configured to have a default off mode in which the device does not deliver therapy to the user, and be configured to change from the off mode to an on mode for the predetermined time period during which the device delivers the therapy to the user before returning to the off mode. Further, triggering delivery of the therapy at generally unpredictable intervals, e.g., whenever the user ingests a meal, can help prevent the user's body from adapting to a particular therapy by learning to expect the therapy at certain times.

The controlled device 108 can be defaulted to a dormant mode until triggered by detected meal intake. Various exemplary embodiments of devices having a dormant mode, as well as various exemplary embodiments of powering a system including a sensor and of transmitting signals, are described in further detail in U.S. Pat. Pub. No. 2010/0056948 filed Aug. 25, 2009 entitled "Stimulation Of Satiety Hormone Release" and U.S. Pat. Pub. No. 2009/0192404 filed Jan. 28, 2008 entitled "Methods And Devices For Measuring Impedance In A Gastric Restriction System." Exemplary controlled devices are disclosed in U.S. Pat. Pub. No. 2012/0172792 filed Dec. 29, 2010 entitled "Obesity Therapy And Heart Rate Variability."

Electrical Stimulation

In some embodiments, the controlled device 108 can be configured to deliver electrical stimulation to the user's tissue, e.g., a stomach wall of the user, an intestinal wall of the user, individual nerves or nerve bundles innervating a target tissue of interest, etc., e.g., for the treatment of obesity and/or co-morbidities.

Because the controlled device 108 can be configured to intermittently deliver stimulation therapy to the user only when triggered by detected meal intake, nerve and/or tissue desensitization to electrical signals and nerve and/or tissue damage can be reduced, if not entirely prevented, because the electrical signal is not continuously delivered to the nerve and/or tissue. Moreover, when triggered to begin delivery of the stimulation therapy by the computer system 106, the controlled device 108 can be configured to non-continuously deliver the electrical signal to the user such that the signal is alternately "off" and "on" when the controlled device 108 is in the on mode. The periods of time in which the signal is "off" and "on" can be the same or different from one another. In exemplary embodiments, the signal can be "off" for a longer period of time than it is "on," which can help reduce, if not prevent, nerve and/or tissue desensitization to electrical signals and nerve and/or tissue damage. Delivering an electrical signal that is "off" for a longer period of time than it is "on" can also help conserve power, e.g., reduce battery consumption, and can reduce the size of a power supply required to power the controlled device 108. However, the controlled device 108 can be configured to continuously deliver the electrical signal to the user, e.g., continuously delivered indefinitely or continuously delivered during a predetermined time period of "N" minutes after the computer system 106 triggers the controlled device 108.

The electrical signal can be applied to more than one location on tissue, e.g., gastrointestinal tissue, of the user. For example, the electrical signal can be applied to two, three, four, or more locations in a distal ileum of the user. A "location" can be defined by the area of physical contact between the tissue and a means for delivery of the electrical stimulus, e.g., a first electrode of the controlled device 108. Accordingly, the application of the electrical signal to a second location on the tissue of the user can include contacting a second electrode of the controlled device 108 with a portion of the tissue that is not in physical contact with the first electrode also electrically stimulating the user.

The electrical signal can have a variety of configurations. Exemplary electrical parameters of the electrical signal that can be varied include frequency, voltage, current, and pulse duration. The electrical signal can have a frequency of about 0.1 Hz to about 90 Hz; for example, the electrical signal can have a frequency of about 0.1 Hz, about 0.15 Hz, about 0.2 Hz, about 0.4 Hz, about 1 Hz, about 4 Hz, about 10 Hz, about 20 Hz, about 25 Hz, about 30 Hz, about 35 Hz, about 40 Hz, about 50 Hz, about 70 Hz, or about 90 Hz. The electrical signal can have a voltage of about 0.5 V to about 25 V; for example, the voltage can be about 1 V, about 2 V, about 5 V, about 10 V, about 14V; about 15 V, about 20 V, or about 25 V. The electrical signal can have a current between about 2 mA and about 10 mA. The electrical signal can have a pulse duration of about 3 ms to about 500 ms; for example, the pulse duration may be about 5 ms, about 50 ms, about 100 ms, about 150 ms, about 200 ms, about 250 ms, about 300 ms, about 350 ms, about 400 ms, about 450 ms, or about 500 ms. In some embodiments, the electrical signal can be applied at a voltage of about 14V, with a pulse duration of about 5 ms, and at a stimulus frequency of about 20 to about 80 Hz; with respect to such embodiments, the stimulus frequency can be, for example, about 20 Hz, about 40 Hz, or about 80 Hz. In other embodiments, the electrical signal can be applied at a voltage of about 14 V, with a pulse duration of about 300 ms, and at a frequency of about 0.4 Hz. Various exemplary embodiments of an electrical signal that can be delivered to a user are described in more detail in U.S. Pat. Pub. No. 2010/0056948 filed Aug. 25, 2009 entitled "Stimulation Of Satiety Hormone Release."

Figure 14:
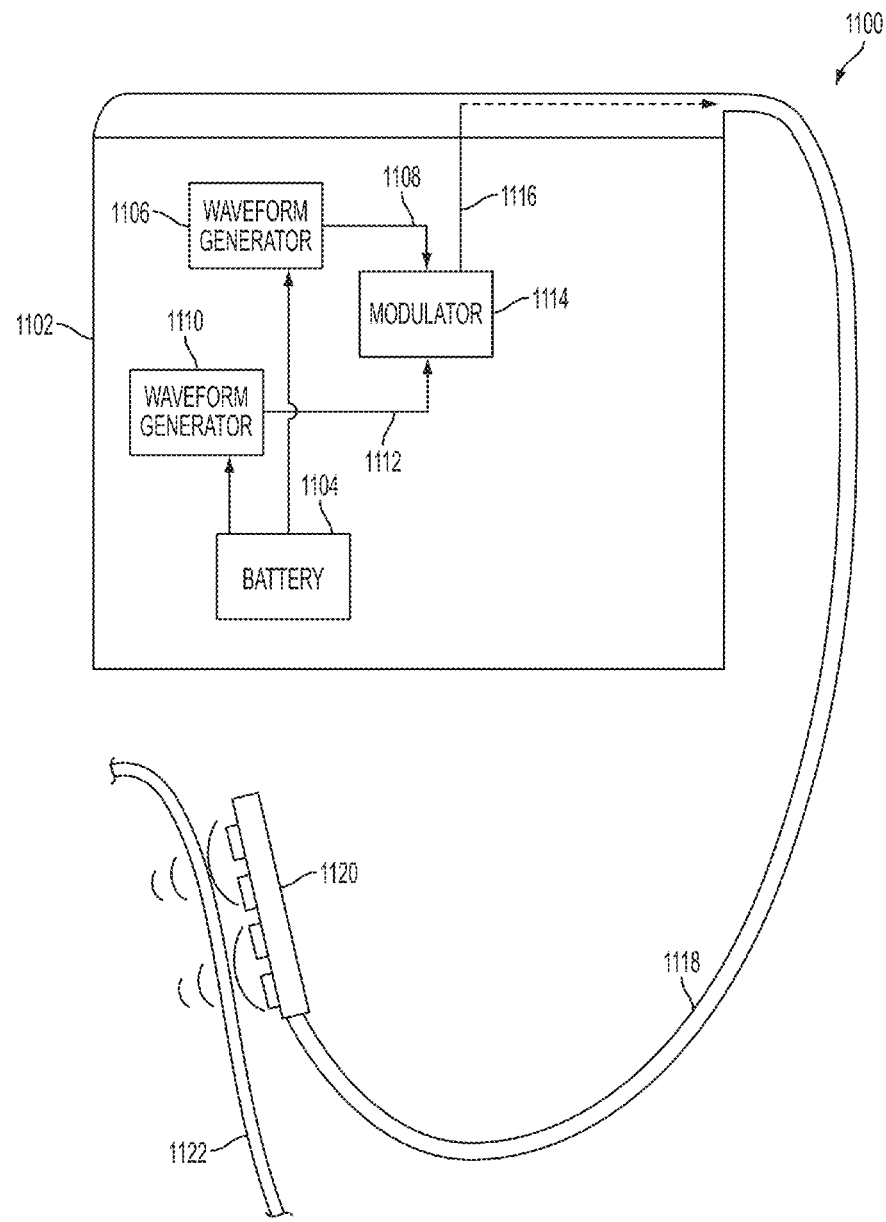
FIG. 14 is a schematic diagram of a controlled device for administering electrical stimulation to a user.

An electrical signal can be delivered to the user in any number of ways to electrically stimulate the user. FIG. 14 illustrates an exemplary embodiment of a controlled device 1100 configured to generate and deliver an electrical signal to a user. Although the illustrated controlled device 1100 is implantable, a controlled device configured to deliver electrical stimulation to a user can be subcutaneously or transcutaneously positioned, as mentioned above. The controlled device 1100 can include a housing 1102 coupled to a suitable power source or battery 1104, such as a lithium battery, a first waveform generator 1106, and a second waveform generator 1108. As in the illustrated embodiment, the battery 1104 and first and second waveform generators can be located within the housing 1102. In other embodiments, a battery can be external to a housing and be wired or wirelessly coupled thereto. The housing 1102 is preferably made of a biocompatible material. The first and second waveform generators 1106, 1108 can be electrically coupled to and powered by the battery 1104. The waveform generators 1106, 1108 can be of any suitable type, such as those sold by Texas Instruments of Dallas, Tex. under model number NE555. The first waveform generator 1106 can be configured to generate a first waveform or low frequency modulating signal 1108, and the second waveform generator 1110 can be configured to generate a second waveform or carrier signal 1112 having a higher frequency than the first waveform 1108. Low frequency modulating signals cannot, in and of themselves, pass through body tissue to effectively stimulate target nerves. The second waveform 1108 can, however, to overcome this problem and penetrate through body tissue. The second waveform 1112 can be applied along with the first waveform 1108 to an amplitude modulator 1114, such as the modulator having the designation On-Semi MC1496, which is sold by Texas Instruments.

The modulator 1114 can be configured to generate a modulated waveform 1116 that is transmitted through a lead 1118 to one or more electrodes 1120. Four electrodes are illustrated, but the device 1100 can include any number of electrodes having any size and shape. The lead 1118 can be flexible, as in the illustrated embodiment. The electrodes 1120 can be configured to, in turn, apply the modulated waveform 1116 to a target tissue or nerve 1122 to stimulate the target 1122. The first and second waveforms 1108, 1112 can have any shape, e.g., the first waveform 1108 can be a square wave, and the second waveform 1112 can be a sinusoidal signal. Although an electrical signal is described that includes carrier and modulating signals, an electrical signal delivered to a user can alternatively include only one of a carrier and modulating signal.

Various exemplary embodiments of methods and devices for delivering an electrical signal to a user are described in more detail in U.S. Pat. Pub. No. 2011/0270360, filed on Dec. 29, 2010 entitled "Methods And Devices For Activating Brown Adipose Tissue," U.S. Pat. Pub. No. 2009/0132018 filed Nov. 16, 2007 entitled "Nerve Stimulation Patches And Methods For Stimulating Selected Nerves," U.S. Pat. Pub. No. 2010/0056948 filed Aug. 25, 2009 entitled "Stimulation Of Satiety Hormone Release," U.S. Pat. Pub. No. 2008/0147146 filed Dec. 19, 2006 entitled "Electrode Patch And Method For Neurostimulation," U.S. Pat. Pub. No. 2005/0277998 filed Jun. 7, 2005 entitled "System And Method For Nerve Stimulation," U.S. Pat. Pub. No. 2006/0195153 filed Jan. 31, 2006 entitled "System And Method For Selectively Stimulating Different Body Parts," U.S. Pat. Pub. No. 2007/0185541 filed Aug. 2, 2006 entitled "Conductive Mesh For Neurostimulation," U.S. Pat. Pub. No. 2006/0195146 filed Jan. 31, 2006 entitled "System And Method For Selectively Stimulating Different Body Parts," U.S. Pat. Pub. No. 2008/0132962 filed Dec. 1, 2006 entitled "System And Method For Affecting Gastric Functions," U.S. Pat. Pub. No. 2008/0147146 filed Dec. 19, 2006 entitled "Electrode Patch And Method For Neurostimulation," U.S. Pat. Pub. No. 2009/0157149 filed Dec. 14, 2007 entitled "Dermatome Stimulation Devices And Methods," U.S. Pat. Pub. No. 2009/0149918 filed Dec. 6, 2007 entitled "Implantable Antenna," U.S. Pat. Pub. No. 2009/0132018 filed Nov. 16, 2007 entitled "Nerve Stimulation Patches And Methods For Stimulating Selected Nerves," U.S. Pat. Pub. No. 2010/0161001 filed Dec. 19, 2008 entitled "Optimizing The Stimulus Current In A Surface Based Stimulation Device," U.S. Pat. Pub. No. 2010/0161005 filed Dec. 19, 2008 entitled "Optimizing Stimulation Therapy Of An External Stimulating Device Based On Firing Of Action Potential In Target Nerve," U.S. Pat. Pub. No. 2010/0239648 filed Mar. 20, 2009 and entitled "Self-Locating, Multiple Application, And Multiple Location Medical Patch Systems And Methods Therefor," and U.S. Pat. Pub. No. 2011/0094773 filed Oct. 26, 2009 entitled "Offset Electrodes."

Various exemplary embodiments of devices configured to directly apply an electrical signal to stimulate nerves are described in more detail in U.S. Pat. Pub. No. 2005/0177067 filed Jan. 26, 2005 entitled "System And Method For Urodynamic Evaluation Utilizing Micro-Electronic Mechanical System," U.S. Pat. Pub. No. 2008/0139875 filed Dec. 7, 2006 entitled "System And Method For Urodynamic Evaluation Utilizing Micro Electro-Mechanical System Technology," U.S. Pat. Pub. No. 2009/0093858 filed Oct. 3, 2007 entitled "Implantable Pulse Generators And Methods For Selective Nerve Stimulation," U.S. Pat. Pub. No. 2010/0249677 filed Mar. 26, 2010 entitled "Piezoelectric Stimulation Device," U.S. Pat. Pub. No. 2005/0288740 filed Jun. 24, 2004 entitled, "Low Frequency Transcutaneous Telemetry To Implanted Medical Device," U.S. Pat. No. 7,599,743 filed Jun. 24, 2004 entitled "Low Frequency Transcutaneous Energy Transfer To Implanted Medical Device," U.S. Pat. No. 7,599,744 filed Jun. 24, 2004 entitled "Transcutaneous Energy Transfer Primary Coil With A High Aspect Ferrite Core," U.S. Pat. No. 7,191,007 filed Jun. 24, 2004 entitled "Spatially Decoupled Twin Secondary Coils For Optimizing Transcutaneous Energy Transfer (TET) Power Transfer Characteristics," and European Pat. Pub. No. 377695 published as Int'l. Pat. Pub. No. WO1989011701 published Nov. 30, 2004 and entitled "Interrogation And Remote Control Device."

Drug Delivery

The controlled device 108 can be configured to administer a therapeutic agent, e.g., a natural or an artificial chemical, solution, active ingredient, nutrient, drug, medicant, nutraceutical, or pharmaceutical to a user.

Figure 15:
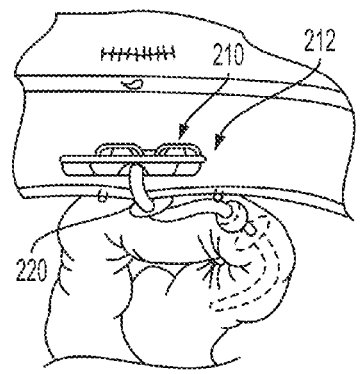
FIG. 15 is a side view of a controlled device for administering a therapeutic agent to a user, the device being shown implanted in the user.

The therapeutic agent can be delivered to the user in any number of ways. FIG. 15 illustrates one exemplary embodiment of a controlled device 108 in the form of a delivery device 212, e.g., an active agent catheter delivery system, configured to deliver a therapeutic agent to a user. The delivery device 212 is shown implanted within an intestine of a user, but the delivery device 212 can be implanted in a variety of locations and can be implanted in a variety of ways, e.g., implanted laparaoscopically, deployed within the colon through a natural orifice procedure, etc. Various exemplary embodiments, including the delivery device 212, of methods and devices for delivering a therapeutic agent to a user are described in more detail in U.S. Pat. Pub. No. 2005/0038415 filed Jul. 12, 2004 entitled "Method And Apparatus For Treatment Of Obesity."

Figure 16:
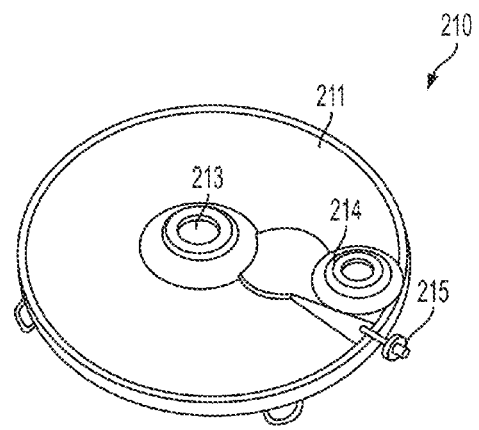
FIG. 16 is a perspective view of a reservoir portion of the controlled device of FIG. 15.

Generally, the delivery device 212 can include an active agent reservoir and pump 210 and an active agent delivery catheter 220. Although any active agent reservoir and pump and active agent delivery catheter can be used, an exemplary embodiment of an active agent reservoir and pump includes a MEDSTREAM™ Programmable Infusion Pump, available from Codman & Shurtleff, Inc. of Raynham, Mass., and an exemplary embodiment of an active agent delivery catheter includes a Codman® silicone tapered arterial catheter, available from Codman & Shurtleff, Inc. The reservoir and pump 210 can include any suitable reservoir and/or fluid delivery pump, e.g., having, as shown in FIG. 16, a resealable fluid insertion boss 213, a fluid reservoir 211, a fluid pump 214, and a radially extended male fluid delivery port 215.

Figure 17:
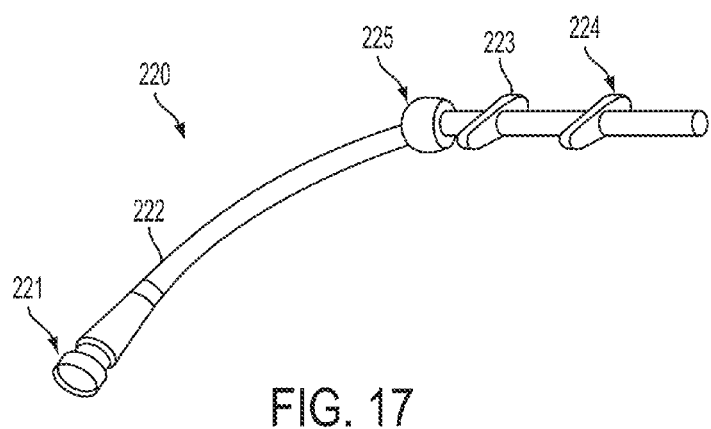
FIG. 17 is a perspective view of a catheter portion of the controlled device of FIG. 15.

In use, a therapeutic agent contained in the reservoir 211 can be dispensed therefrom, through the catheter 220, (e.g., into the ileum of the user in order to decrease intestinal motility and increase feelings of satiety experienced by the user). Optionally, the reservoir 211 can be recharged at any time necessary. Preferably, recharging of the reservoir 211 is performed without removal from the implantation site but is performed transcutaneously such as, for example, by injection with a syringe. The active agent delivery catheter 220, as shown in FIG. 17, can include a female port 221 positioned at a first terminal end of catheter 220 and configured to mate with the male fluid delivery port 215 of the reservoir and pump 210. The catheter 220 can include an elongate fluid transmission lumen 222 extending from the female port 221 to a second terminal end of the catheter 220. Positioned near the second terminal end of the catheter 220 and around a circumference of the lumen 222 can be a first laterally extending brace 223. A second laterally extending brace 224 can be positioned distally to the first laterally extending brace 223 in close proximity to the second terminal end of the catheter 220. The catheter 220 can also include a balloon 225 configured to secure the catheter 220 within, e.g., the user's abdominal cavity, wherein a securing means, such as a row of pursestring sutures, can be placed and tightened around an opening in the intestine to secure the intestine to the catheter 220. The balloon 225 can then be pulled taut against the sealing means to prevent leakage of intestinal contents.

Ileal Brake Nutrients

The controlled device 108 can be configured to administer any substance (e.g., a nutrient) configured to provoke a release of one or more hormones from L-cells, such as linoleic acid (LA), a carbohydrate, other sugars, an amino acid, a protein, a fatty acid, a fat, or any combination thereof. The nutrient can take the form of a natural food item; a supplement, e.g., a nutrition drink; or a substance that is made with the express purpose of stimulating L-cells, and therefore need not be a "nutrient" per se in the conventional sense. Generally, delivery of the nutrient to the user, such as to the user's intestine, e.g., an ileum of the intestine, can help trigger ileal brake. Normally, the presence of nutrients, which arise from a meal consisting of carbohydrates, fats and proteins, termed "digesta" in the digestive tract, stimulates release of the body's own incretins into the blood stream. Key hormones, released by specialized L-cells located in the mucosa, which is the innermost interior (luminal) wall of the intestines, coordinate the body's response to a meal. The hormones produce this effect by inducing a sense of fullness and cessation of eating (satiety), triggering the release of insulin to maintain proper glucose levels (incretin effect) and slowing the passage of contents through the digestive tract (delaying gastric emptying and slowing small intestinal transit). Collectively, these effects have been termed the ileal brake. By delivering the nutrient, e.g., triggering ileal brake, at the onset of the user ingesting a meal, satiation can occur earlier than it would in a normal digestive process without the delivery of the nutrient to the user. The user can therefore feel full faster after beginning to eat, thereby encouraging smaller amounts of food intake and, over time, encouraging weight loss. Triggering ileal brake and various exemplary embodiments of nutrients and administration thereof to a user to help treat obesity are described in more detail in U.S. Pat. Pub. No. 2010/0056948 filed Aug. 25, 2009 entitled "Stimulation Of Satiety Hormone Release."

Insulin

The controlled device 108 can be an insulin pump, continuous glucose meter, or artificial pancreas. Meal detection using the meal detection system 100 described herein can be used with the insulin pump or artificial pancreas to control insulin release, instead of or in addition to the continuous blood glucose sensors that are typically used. The system 100 can allow for earlier triggering than relying solely on measurement of interstitial glucose. The system 100 can also allow for less frequent blood glucose sampling, allowing for a more dormant duty cycle to increase battery life. The system 100 can detect when exercise is occurring (e.g., by detecting sustained elevated heart rate or repeated body movements consistent with running or exercising), which can be considered in determining the timing and quantity of insulin delivery. The system 100 can also allow for meal size or meal duration to be estimated, and can be used to maintain a log of meal intake for user education, accountability, or awareness. Exemplary insulin pumps and/or artificial pancreases are disclosed in U.S. Pat. No. 4,515,584 issued on May 7, 1985 entitled "Artificial Pancreas"; U.S. Pat. No. 6,023,009 issued on Feb. 8, 2000 entitled "Artificial Pancreas"; and U.S. Pat. No. 8,346,399 issued on Jan. 1, 2013 entitled "Programmable Insulin Pump." It will be appreciated that any of the devices or methods disclosed in the foregoing references can be modified in accordance with the teachings herein to trigger insulin release in response to meal intake detected by the computer system 106.

Bile Acid Modulation

The controlled device 108 can be configured to deliver a composition effective to modulate bile acid levels in the user, e.g., to treat a metabolic disorder. Exemplary methods and devices for modulating bile acid are disclosed in U.S. application Ser. No. 13/631,095, filed on Sep. 28, 2012 and entitled "Methods and Compositions of Bile Acids." It will be appreciated that any of the devices or methods disclosed in the foregoing reference can be modified in accordance with the teachings herein to modulate bile acid levels based on meal intake detected by the computer system 106.

pH Therapy

The controlled device 108 can be configured to deliver a composition, e.g., bicarbonate, effective to modulate pH in the user's stomach or in other portions of the user's digestive tract. For example, the device 108 can be configured to release a composition to increase gastric pH during meal intake when said intake is detected by the computer system 106. Increasing the pH can prevent certain digestive enzymes responsible for breaking down proteins, such as pepsin, from being activated. In some embodiments, the device 108 can modulate gastric pH during meal intake to a level of at least about 2.4, at least about 3, at least about 5, and/or at least about 7.

Other Drugs

The controlled device 108 can be configured to deliver other drugs, including GLP-1 agonists (e.g., exenatide ("Byetta") or liraglutide ("Victoza")), activators of Brown Adipose Tissue (e.g., norepinephrine, etc.), Melanocortin Four Receptor Agonists, and other agents that impact metabolic function.

Aversive Response

The controlled device 108 can be configured to cause or provoke an aversive response in the user when the user exceeds a certain threshold of meal intake (e.g., to discourage the user from overeating). The threshold can be defined by meal onset, meal volume, meal content (type of food), intake rate, meal duration, and/or meal conclusion. The aversive therapy can be mechanical, electrical, and/or chemical in nature. Exemplary aversive responses include satiety, upset stomach, vomiting, diarrhea, abdominal cramps, nausea, and audible or visual user notifications. For example, the controlled device 108 can be configured to deliver lithium chloride to the user when the computer system 106 detects that the meal volume or meal duration has exceeded a threshold. The meal volume or duration threshold can be based on a variety of factors, including a normal or prescribed caloric intake for the user. Exemplary devices and methods for creating aversive responses in the form of satiety, upset stomach, vomiting, abdominal cramps, nausea, and audible or visual user notifications are disclosed in International Publication No. WO2009096859 entitled "A Device For Treating Obesity," International Publication No. WO2006034400 entitled "Responsive Gastric Stimulator," International Publication No. WO2006049725 entitled "Surgical Systems And Devices To Enhance Gastric Restriction Therapies," U.S. Pat. Pub. No. 2006/0020298 entitled "Systems and Methods for Curbing Appetite," U.S. Pat. Pub. No. 2004/0147816 entitled "Analysis Of Eating Habits," and International Publication No. WO0226101 entitled "System And Method For The Control Of Behavioral Disorders," respectively.

GLP-1 Release Stimulation

The controlled device 108 can be configured to apply mechanical or electrical stimulation to stimulate the release of GLP-1 through L-cells in the small intestines, e.g., to treat type 2 diabetes. Exemplary devices and methods for stimulating GLP-1 release are disclosed in International Application Nos. PCT/EP2012/055795, PCT/EP2012/055834, PCT/EP2012/055798, PCT/EP2012/055844, and PCT/EP2012/055831. It will be appreciated that any of the devices or methods disclosed in the foregoing references can be modified in accordance with the teachings herein to stimulate GLP-1 release in response to meal intake detected by the computer system 106.

Brown Adipose Tissue Activation (Bat)

The controlled device 108 can be configured to activate brown adipose tissue, for example using electrical stimulation as disclosed in U.S. Pat. Pub. No. 2011/0270360, filed on Dec. 29, 2010 entitled "Methods And Devices For Activating Brown Adipose Tissue Using Electrical Energy." The meal detection system 100 can trigger BAT activation immediately after a meal when calories are readily available for consumption in the blood stream, which can improve the effectiveness of the BAT activation. Linking treatment to meal intake can also minimize overall stimulation time, prolonging battery life, allowing for smaller devices, and delaying the body's adaptation to the therapy.

Gastric Bands

The controlled device 108 can be a gastric band or a device configured to adjust a gastric band. Adjustable gastric band devices and related methods are disclosed in U.S. Pat. Pub. No. 2009/0204132, filed on Feb. 12, 2008 entitled "Automatically Adjusting Band System." It will be appreciated that any of the devices or methods disclosed in the foregoing reference can be modified in accordance with the teachings herein to adjust a gastric band based on meal intake detected by the computer system 106, e.g., to tighten the band or increase the restriction provided by the band when meal intake is detected or when meal intake that exceeds a particular volume or duration threshold is detected.

Gastric Pacing

The controlled device 108 can be configured to control the tonal contractions of the stomach to affect one or more physiological parameters. For example, the tonal contractions can be controlled to speed up or slow down gastric emptying, or to induce nausea, satiety, and the like. Exemplary methods and devices for gastric pacing are disclosed in U.S. Pat. No. 8,239,027, issued on Aug. 7, 2012 entitled "Responsive Gastric Stimulator." It will be appreciated that any of the devices or methods disclosed in the foregoing reference can be modified in accordance with the teachings herein to adjust the gastric pacing based on meal intake detected by the computer system 106.

Gastric Space Occupying Devices

The controlled device 108 can be a gastric space and/or volume occupying device (e.g., a gastric balloon) or a device configured to adjust a gastric space and/or volume occupying device. Adjustable gastric balloons and related methods are disclosed in U.S. Pat. No. 8,236,023 issued on Aug. 7, 2012 entitled "Apparatus And Method For Volume Adjustment Of Intragastric Balloons." It will be appreciated that any of the devices or methods disclosed in the foregoing reference can be modified in accordance with the teachings herein to adjust a gastric space occupying device based on meal intake detected by the computer system 106, e.g., to increase the volume of the device when meal intake is detected or when meal intake that exceeds a particular volume or duration threshold is detected.

Gastric Emptying

A number of methods and devices have been developed for changing the rate of gastric emptying in a user. Exemplary methods and devices for altering gastric emptying rates include pyloric shuttles, pyloric valves, and electrical stimulation devices for altering pyloric function. Pyloric shuttles are disclosed in U.S. Pat. No. 8,048,169 issued on Nov. 1, 2011 entitled "Pyloric valve obstructing devices and methods." Pyloric valves are disclosed in U.S. Pat. No. 8,182,442 issued on May 22, 2012 entitled "Pyloric valve devices and methods" and in U.S. Publication No. 2012/0259427 filed on Jun. 22, 2012 entitled "Pyloric Valve." Electrical stimulation devices for altering pyloric function are disclosed in International Publication No. WO/2005/041749. Additional details on gastric emptying can be found in Melissa, J, Leventi, A, Klinaki, I, et al. "Alterations of global gastrointestinal motility after sleeve gastrectomy: A prospective study." Ann Surg 2012. It will be appreciated that any of the devices or methods disclosed in the foregoing references can be modified in accordance with the teachings herein to adjust a rate of gastric emptying based on meal intake detected by the computer system 106, e.g., to increase or decrease the rate of gastric emptying when meal intake is detected or when meal intake that exceeds a particular volume or duration threshold is detected Pattern Recording and Recognition The controlled device 108 can be configured to record and analyze meal intake patterns and/or issue user reminders. For example, each time the computer system 106 detects that meal intake is occurring, the controlled device 108 can remind the user to test blood glucose. By way of further example, the controlled device 108 can store a record of the meal intake event. The record can include various information, including the date and time at which meal intake occurred, the sensor data at the time of meal intake (e.g., the user's heart rate, temperature, etc.), the time duration of the meal intake event, the estimated volume of the meal intake event, and so forth.

The controlled device 108 can use stored records of meal intake events to issue alerts to the user that a threshold amount of meal intake has been exceeded, or that a deviation from a meal intake routine has occurred. In insulin-dependent users, for example, following a certain discipline or meal intake pattern in the user's daily lifestyle can help keep the user's condition under control. Stress, travel, and other things, however, can lead to deviations from this pattern, in which case the controlled device 108 can be configured to alert the user to the deviation (e.g., by emitting a visible or audible alert). A saved history of meal intake events can also be helpful in cases where hyperglycaemia or hypoglycaemia occur, as the user can review their meal intake history on the controlled device 108 to understand what went wrong. Less-independent insulin users can also benefit from meal intake logging, as their caregivers can review and monitor the user's meal intake patterns. In highly-dependent insulin patients (e.g., children) the controlled device 108 can be configured to send an email, text message, or other alert to the patient's caretaker (e.g., parents) who can in turn reinforce timely glucose metering and, if necessary, insulin administration (e.g., by sending instructions or a reminder to the child at school). Generally speaking, meal intake logging and monitoring can provide the user with increased awareness of their meal intake patterns, which can be helpful in treating various conditions including obesity and diabetes.

The controlled device 108 can also be configured to remind the user to test blood glucose levels, or to provide some other alert, when the computer system 106 detects that exercise has occurred or is occurring (e.g., by detecting an elevated heart rate from the ECG sensor or accelerometer data indicative of exercise).

Combinations

It will be appreciated that the controlled device 108 can be configured to perform a combination of any of the functions described above, and/or to deliver a combination of the therapies described above. For example, the controlled device 108 can be configured to deliver both a nutrient and electrical stimulation to the user. As described in further detail in U.S. Pat. Pub. No. 2010/0056948 filed Aug. 25, 2009 entitled "Stimulation Of Satiety Hormone Release," delivering a nutrient to a user and electrically stimulating the user can cause a higher expression of Glucagon-Like Peptide (GLP-1), and hence enhance triggering of ileal brake, than delivery of the nutrient to the user without electrical stimulation. By triggering delivery of the nutrient and the electrical stimulation relatively quickly after meal intake begins through the triggering of the controlled device 108 by the computer system 106, ileal brake can be further encouraged in a faster fashion than would naturally occur or that would occur if the nutrient was delivered without electrical stimulation. In an exemplary embodiment, and as further discussed in U.S. Pat. Pub. No. 2010/0056948, the electrical signal can be delivered to a tissue of the user contemporaneously with the contacting of L-cells of the tissue with the nutrient delivered to the user. "Contemporaneously" generally means that during at least part of the time that the electrical signal is being delivered to the tissue, the L-cells are in direct contact with the nutrient. Thus, if the electrical signal is delivered for a total duration of one second, contacting the L-cells with the nutrient stimulus for 5 seconds after the application of the electrical signal and for 0.1 seconds during the application of the electrical signal will be considered to have been contemporaneous with the application of the electrical signal.

In some embodiments, a nutrient can be orally administered to a user, e.g., the user can swallow a nutrient, e.g., as a pill, a fluid, etc., in conjunction with meal intake, e.g., at a start of a meal. Stimulation of the user's L-Cells can be enhanced by electrical stimulation of the user in the presence of the nutrient, e.g., by the controlled device 108 delivering an electrical signal to the user. In other embodiments, a meal that a user ingests can serve as a stimulus for the user's L-Cells, which can be amplified by triggered delivery of electrical stimulation to the user. Since meals can serve to stimulate L-cell production of GLP-1, when properly timed, the electrical stimulation can begin as the meal transits into the user's duodenum. There is a feed forward signal to the ileum which is responsible for increase in GLP-1 production. This can be enhanced by the presence of electrical stimulation in the intestine.

Concluding Remarks

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination, e.g., electrodes, a battery or other power source, an externally wearable sensor and/or housing therefor, etc. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

In some embodiments, devices described herein can be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A meal detection system, comprising:
a plurality of sensors, each configured to sense a different physiological parameter of a user, the plurality of sensors being disposed external to the user;
a processor in communication with the plurality of sensors and configured to analyze outputs of the plurality of sensors to detect meal intake by the user, the processor being further configured to trigger a controlled device to deliver a therapy to the user in response to meal intake detected by the processor;
wherein, for each of the plurality of sensors, the processor is configured to calculate an index based on the output of the sensor and to determine that meal intake occurred when the index exceeds a threshold value; and
wherein the processor is configured to calculate the threshold value by processing a set of training data usin an average harmonic mean algorithm, the training data including sensor data for at least one user and ground truth data for the at least one user.

2. The system of claim 1, wherein the plurality of sensors are of different types.

3. The system of claim 1, wherein the plurality of sensors includes an electromyograph configured to detect electrical activity of a muscle of the user and wherein the processor is configured to calculate an electromyograph index based on a number of peaks detected in the electromyograph output.

4. The system of 1, wherein the plurality of sensors includes a microphone configured to detect sounds emitted by the user and wherein the processor is configured to calculate a microphone index based on frequency matching and temporal matching of the microphone output to a predetermined pattern.

5. The system of claim 1, wherein the plurality of sensors includes an electrocardiograph configured to detect electrical activity of a heart of the user and wherein the processor is configured to calculate an electrocardiograph index based on a moving average filtered first derivative of the standard deviation of interbeat intervals in the electrocardiograph output.

6. The system of claim 1, wherein the plurality of sensors includes a temperature sensor configured to detect a temperature of the user and wherein the processor is configured to calculate a temperature sensor index based on a ratio of low frequency components of the first derivative of the temperature sensor output to low frequency components of the standard deviation of the temperature sensor output.

7. The system of 1, wherein the plurality of sensors includes an accelerometer configured to detect motion of the user and wherein the processor is configured to calculate an accelerometer index based on the total energy of the accelerometer output in a frequency band of interest.

8. The system of claim 1, wherein the plurality of sensors includes an electrogastrograph configured to detect electrical activity of a digestive system of the user and wherein the processor is configured to calculate an electrogastrograph index based on the total energy of the electrogastrograph output in a frequency band of interest.

9. The system of claim 1, wherein the plurality of sensors includes an impedance sensor configured to detect an impedance across a portion of the user and wherein the processor is configured to calculate an impedance sensor index based on the median energy of the impedance sensor output in a frequency band of interest.

10. The system of claim 1, further comprising a controlled device, the controlled device being configured to at least one of:
electrically stimulate tissue of the user;
deliver a therapeutic agent to the user;
deliver a therapeutic agent configured to provoke a release of one or more hormones from L-cells of the user to trigger ileal brake in the user;
deliver insulin to the user;
modulate bile acid levels in the user;
modulate gastric pH levels in the user;
induce an aversive response in the user;
stimulate release of GLP-1 in the user;
activate brown adipose tissue in the user;
adjust a gastric band implanted in the user;
control tonal contractions of the user's stomach;
adjust a size or volume of a gastric space occupying device implanted in the user;
modulate gastric emptying in the user;
record a history of the user's meal intake events; and
issue an alert to the user or to a caregiver of the user when the user's meal intake exceeds a predetermined threshold or deviates from a predetermined pattern.

11. A meal detection system, comprising:
a plurality of sensors, each configured to sense a different physiological parameter of a user, the plurality of sensors being disposed external to the user; and
a processor in communication with the plurality of sensors and configured to analyze outputs of the plurality of sensors to detect meal intake by the user, the processor being further configured to trigger a controlled device to deliver a therapy to the user in response to meal intake detected by the processor,
wherein the plurality of sensors includes an electromyograph and an accelerometer, and wherein the processor is configured to calculate an electromyograph index, an electromyograph threshold value, an accelerometer index, and an accelerometer threshold value, and to determine that:
solid meal intake occurred when the electromyograph index exceeds the electromyograph threshold value;
liquid meal intake occurred when the electromyograph index does not exceed the electromyograph threshold value and the accelerometer index exceeds the accelerometer threshold value; and no meal intake occurred when the electromyograph index does not exceed the electromyograph threshold value and the accelerometer index does not exceed the accelerometer threshold value.

12. A meal detection system, comprising:

a plurality of sensors, each configured to sense a different physiological parameter of a user, the plurality of sensors being disposed external to the user; and a processor in communication with the plurality of sensors and configured to analyze outputs of the plurality of sensors to detect meal intake by the user, the processor being further configured to trigger a controlled device to deliver a therapy to the user in response to meal intake detected by the processor, wherein the plurality of sensors includes an impedance sensor and an accelerometer, and wherein the processor is configured to calculate an impedance sensor index, an impedance sensor threshold value, an accelerometer index, and an accelerometer threshold value, and to determine that:

solid meal intake occurred when the impedance sensor index exceeds the impedance sensor threshold value;

liquid meal intake occurred when the impedance sensor index does not exceed the impedance sensor threshold value and the accelerometer index exceeds the accelerometer threshold value; and no meal intake occurred when the impedance sensor index does not exceed the impedance sensor threshold value and the accelerometer index does not exceed the accelerometer threshold value.

13. A meal detection system, comprising:

a plurality of sensors, each configured to sense a different physiological parameter of a user, the plurality of sensors being disposed external to the user; and a processor in communication with the plurality of sensors and configured to analyze outputs of the plurality of sensors to detect meal intake by the user, the processor being further configured to trigger a controlled device to deliver a therapy to the user in response to meal intake detected by the processor, wherein the plurality of sensors includes an electromyograph and a microphone, and wherein the processor is configured to calculate an electromyograph index, an electromyograph threshold value, a microphone index, and a microphone threshold value, and to determine that:

solid meal intake occurred when the electromyograph index exceeds the electromyograph threshold value;

liquid meal intake occurred when the electromyograph index does not exceed the electromyograph threshold value and the microphone index exceeds the microphone threshold value; and no meal intake occurred when the electromyograph index does not exceed the electromyograph threshold value and the microphone index does not exceed the microphone threshold value.

14. A meal detection system, comprising:

a plurality of sensors, each configured to sense a different physiological parameter of a user, the plurality of sensors being disposed external to the user; and a processor in communication with the plurality of sensors and configured to analyze outputs of the plurality of sensors to detect meal intake by the user, the processor being further configured to trigger a controlled device to deliver a therapy to the user in response to meal intake detected by the processor, wherein the plurality of sensors includes an impedance sensor and a microphone, and wherein the processor is configured to calculate an impedance sensor index, an impedance sensor threshold value, a microphone index, and a microphone threshold value, and to determine that:

solid meal intake occurred when the impedance sensor index exceeds the impedance sensor threshold value and the microphone index exceeds the microphone threshold value;

liquid meal intake occurred when the impedance sensor index does not exceed the impedance sensor threshold value and the microphone index exceeds the microphone threshold value; and no meal intake occurred when the impedance sensor index does not exceed the impedance sensor threshold value and the microphone index does not exceed the microphone threshold value.

15. A medical method, comprising:

sensing a plurality of physiological parameters of a user using a plurality of sensors disposed externally to the user;

using a processor in communication with the plurality of sensors, analyzing outputs of the plurality of sensors to detect meal intake by the user; and automatically triggering a controlled device to deliver a therapy to the user in response to meal intake detected by the processor;

for each of the plurality of sensors, using the processor o calculate an index based on the output of the sensor and using the processor to determine that meal intake occurred when the index exceeds a threshold value; and using the processor to calculate the threshold value by processing a set of training data using an average harmonic mean algorithm, the training data including sensor data for at least one user and ground truth data for the at least one user.

16. The method of claim 15, wherein said sensing and said analyzing include at least one of:

detecting electrical activity of a muscle of the user using an electromyograph and calculating an electromyograph index based on a number of peaks detected in the electromyograph output;

detecting sounds emitted by the user using a microphone and calculating a microphone index based on frequency matching and temporal matching of the microphone output to a predetermined pattern;

detecting electrical activity of a heart of the user using an electrocardiograph and calculating an electrocardiograph index based on a moving average filtered first derivative of the standard deviation of interbeat intervals in the electrocardiograph output;

detecting a temperature of the user and calculating a temperature sensor index based on a ratio of low frequency components of the first derivative of the temperature sensor output to low frequency components of the standard deviation of the temperature sensor output;

detecting motion of the user using an accelerometer and calculating an accelerometer index based on the total energy of the accelerometer output in a frequency band of interest;

detecting electrical activity of a digestive system of the user using an electrogastrograph and calculating an electrogastrograph index based on the total energy of the electrogastrograph output in a frequency band of interest; and detecting an impedance across a portion of the user using an impedance sensor and calculating an impedance sensor index based on the median energy of the impedance sensor output in a frequency band of interest.

17. The method of claim 15, wherein triggering the controlled device comprises causing the controlled device to at least one of:
    electrically stimulate tissue of the user;
    deliver a therapeutic agent to the user;
    deliver a therapeutic agent configured to provoke a release of one or more hormones from L-cells of the user to trigger ileal brake in the user;
    deliver insulin to the user;
    modulate bile acid levels in the user;
    modulate gastric pH levels in the user;
    induce an aversive response in the user;
    stimulate release of GLP-1 in the user;
    activate brown adipose tissue in the user;
    adjust a gastric band implanted in the user;
    control tonal contractions of the user's stomach;
    adjust a size or volume of a gastric space occupying device implanted in the user;
    modulate gastric emptying in the user;
    record a history of the user's meal intake events; and
    issue an alert to the user or to a caregiver of the user when the user's meal intake exceeds a predetermined threshold or deviates from a predetermined pattern.

18. The method of claim 15, wherein said sensing comprises detecting an impedance across a portion of the user using an impedance sensor having a first current electrode, a second current electrode, a first voltage electrode, and a second voltage electrode, and wherein the method further comprises at least one of:
    positioning the first current electrode on the user's left trapezius muscle, positioning the second current electrode on the user's right trapezius muscle, positioning the first voltage electrode on the user's chest below the user's left clavicle and about half way between the user's neck and the user's left shoulder, and positioning the second voltage electrode on the user's chest below the user's right clavicle and about half way between the user's neck and the user's right shoulder; and
    positioning the first current electrode on the user's chest below the user's left clavicle and about half way between the user's neck and the user's left shoulder, positioning the second current electrode on the user's chest below the user's right clavicle and about half way between the user's neck and the user's right shoulder, positioning the first voltage electrode beneath the first current electrode and inward towards the user's sternum, and positioning the second voltage electrode beneath second current electrode and inward towards the user's sternum.

* * * * *